United States Patent
Blanc-Brude et al.

(10) Patent No.: US 8,828,724 B2
(45) Date of Patent: Sep. 9, 2014

(54) METHOD FOR PREPARING CELLS FOR ENGRAFTMENT

(75) Inventors: Olivier Blanc-Brude, Paris (FR); Arnaud Bonnefoy, Montreal (CA)

(73) Assignee: Institut National de la Sante et de la Recherche Medicale (Inserm), Paris (FR)

( * ) Notice: Subject to any disclaimer, the term of this patent is extended or adjusted under 35 U.S.C. 154(b) by 660 days.

(21) Appl. No.: 12/665,791

(22) PCT Filed: Aug. 14, 2008

(86) PCT No.: PCT/EP2008/060714
§ 371 (c)(1),
(2), (4) Date: Dec. 21, 2009

(87) PCT Pub. No.: WO2009/024538
PCT Pub. Date: Feb. 26, 2009

(65) Prior Publication Data
US 2010/0173352 A1     Jul. 8, 2010

(30) Foreign Application Priority Data
Aug. 17, 2007 (EP) .................................. 07291022

(51) Int. Cl.
| | | |
|---|---|---|
| C12N 5/00 | (2006.01) | |
| C12N 5/02 | (2006.01) | |
| C07K 14/00 | (2006.01) | |
| A61K 38/00 | (2006.01) | |
| A61K 38/39 | (2006.01) | |
| C12N 5/0775 | (2010.01) | |

(52) U.S. Cl.
CPC ............ *A61K 38/39* (2013.01); *C12N 2533/54* (2013.01); *C12N 2533/56* (2013.01); *C12N 5/0663* (2013.01); *C12N 2501/585* (2013.01)
USPC ............................ 435/375; 435/377; 530/300

(58) Field of Classification Search
None
See application file for complete search history.

(56) References Cited

U.S. PATENT DOCUMENTS 5,399,667 A    3/1995  Frazier et al.

OTHER PUBLICATIONS

Blanc-Brude et al ( Circulation, 2007, v.116, p. 175).*
Ii et al ( Circ. Res. 2006,v.98, pp. 697-704).*
Bailey Dubose et al ( The University of Alabama at Birmingham Dissertation Abstracts International, (2006) vol. 67, No. 7B, p. 3933).*
Mikayama et al. PNAS, 1993. 90: 10056-10060.*
Burgess et al .J Cell Biol. 111:2129-2138, 1990.*
Wang et al. JBC, 2001 276:49213-49220.*
Ngo et al, in The Protein Folding Problem and Tertiary Structure Prediction, 1994. (ed.), Birkhauser, Boston, MA, pp. 433 and 492-495.).*
International Search Report and Written Opinion of the Searching Authority for PCT/EP2008/060714.
Schroeter Marco et al: "The adipokine leptin promotes integrin-mediated adhesion of endothelial progenitor cells" Circulation, vol. 114, No. 18, Suppl. S, (Oct. 2006), p. 121.
Narizhneva Natalya V et al: "Thrombospondin-1 up-regulates expression of cell adhesion molecules and promotes monocyte binding to endothelium" FASEB Journal, vol. 19, No. 6, (Apr. 2005).
Bagley R G et al: "Endothelial Precursor Cells as a Model of Tumor Endothelium: Characterization and Comparison with Mature Endothelial Cells" Cancer Research, American Association for Cancer Research, Baltimore, MD, US, vol. 63, No. 18, 2003, pp. 5866-5873.
Barazi Heba 0 et al: "Regulation of integrin function by CD47 ligands. Differential effects on alphavbeta3 and alpha4beta1 integrin-mediated adhesion." Journal of Biological Chemistry, vol. 277, No. 45, (Nov. 8, 2002), pp. 42859-42866.
Aicher Alexandra et al: "Assessment of the tissue distribution of transplanted human endothelial progenitor cells by radioactive labeling." Circulation, vol. 107, No. 16, (Apr. 29, 2003), pp. 2134-2139.
Brown Eric J et al: "Integrin-associated protein (C047) and its ligands" Trends in Cell Biology, Elsevier Science Ltd, XX, vol. 11, No. 3, (Mar. 2001), pp. 130-135.
Isenberg et al, "CD47 is Necessary for Inhibition of Nitric Oxide-stimulated Vasulcar Cell Responses by Thrombospondin-1* ", Sep. 8, 2006, pp. 26069-26080, vol. 281, No. 36, The Journal of Biological Chemistry.
Werner et al, "Influence of Cardiovascular Risk Factors on Endothelial Progenitor Cells: Limitations for Therapy?", 2006, pp. 257-266, vol. 26, Arteriosclerosis, Thrombosis, and Vascular Biology.
Isenberg et al, "Increasing Survival of Ischemic Tissue by Targeting CD47", 2007, pp. 712-720, vol. 100, Circulation Research.
Babic et al, "SHPS-1 Induces Aggregation of Ba/F3 Pro-B Cells Via an Interaction with CD47", 2000, pp. 3652-3658, vol. 164, Journal of Immunology.
Freyberg et al, "Proatherogenic Flow Conditions Initiate Endothelial Apoptosis via Thrombospondin-1 and the Integrin-Associated Protein", 2001, pp. 141-149, vol. 286, Biochemical and Biophysical Research Communications.
Loomans et al, "Endothelial Progenitor Cell Dysfunction in Type 1 Diabetes: Another Consequence of Oxidative Stress?" 2005, pp. 1468-1475, vol. 7, Antioxidants & Redox Signaling.
Kanda et al, "Role of Thrombospondin-1-Derived Peptide, 4N1K, in FGF-2-Induced Angiogenesis", 1999, pp. 262-272, vol. 252, Experimental Cell Research.

* cited by examiner

*Primary Examiner* — Michail Belyavskyi
(74) *Attorney, Agent, or Firm* — B. Aaron Schulman, Esq.; Stites & Harbison, PLLC.

(57) ABSTRACT

The present invention relates to an in vitro method for preparing progenitor cells having an increased adhesivity, wherein progenitor cells are contacted with an agonist of the CD47/IAP receptor thereby yielding progenitor cells presenting an increased adhesivity.

8 Claims, 15 Drawing Sheets

METHOD FOR PREPARING CELLS FOR ENGRAFTMENT

FIELD OF THE INVENTION

The present invention relates to a method for preparing cells for engraftment and to the use of cells liable to be obtained by said method in the frame of regenerative cell therapy.

BACKGROUND OF THE INVENTION

The discovery and better characterization of stem cells in foetal and adult tissues over the last decade has opened novel possibilities for cell therapy. These primitive or incompletely differentiated "progenitor cells", which present high self-renewal capacity, can give rise to fully differentiated cells, or acquire specific differentiated phenotypes once administered to patients. Progenitor cells can be isolated from embryos or adult issues including peripheral blood, bone marrow and adipose tissue for instance, as well as other specialized tissues such as umbilical cord blood.

The increasingly well defined methods for the identification and isolation of progenitor cell populations have strongly encouraged the development of stem cell-based therapy strategies to be deployed clinically. Besides, as a means to circumvent ethical difficulties associated with the use of human foetal tissues, the isolation and transplantation of progenitor cells originating from adult tissues is favoured.

Regenerative cell therapy with progenitor cells seems particularly relevant for diseases in which organs are compromised in such a way that tissue reconstruction is required, e.g. to restore the function of a diseased organ, or when physiological repair mechanisms are impaired.

Thus, one notable field of application of progenitor cell therapy relates to cardiovascular diseases. In these cases, the primary goal is to enhance tissue perfusion by promoting the growth or emergence of a new vascular tree, or to improve the function of existing vessels. Other examples of applications of progenitor cell therapy also include the revascularization and repair of defective heart tissues with vascular progenitors.

In most instances, the progenitor cells of interest are delivered into the general circulation. Current approaches thus rely mostly on the ability of the transplanted cells to directly exert their effects in the circulation, or to find their way to the target tissue, integrate therein and exert their beneficial effects through innate and little understood mechanisms.

In order to maximize the therapeutic effects, local administration of the progenitor cells has also been attempted. It is then hoped that a greater proportion of the transplanted progenitor cells will engraft in the tissue, which would provide enhanced beneficial effects. However, the transplanted cells often fail to adhere to the local substratum, and rapidly clear out of the receiving tissue through mechanisms which remain mostly enigmatic, but seem to include apoptosis.

Thus, the lack of adhesive capacity of the engrafted cells, in particular the lack of specific adhesive capacity for the targeted tissues, may compromise cell engraftment into the targeted tissue and lead to significant loss of the administered cells (Aicher et al. (2003) Circulation 107:2134-9). Administered cells may thus be either destroyed in situ through innate immune response pathways, pass into the blood flow, and get cleared out by organs such as the liver and spleen, or get trapped into lung capillaries, for instance.

Moreover, cell therapy is met with further limitations beyond the engraftment of administered cells into the targeted tissue. The engrafted cells may be ineffective at participating to the reconstruction of the targeted tissue. In particular, the failure of engrafted cells may be due to reduced mid-term and long-term survival, or to the loss of some of their properties, such as their angiogenic and/or vasculogenic activity, e.g. reduced growth factor and cytokine secretion, or their impaired capacity to differentiate and acquire the desired phenotype.

Besides the above-mentioned barriers to cell therapy, other difficulties arise from the pathologies which afflict the individual from whom the cells for engraftment have been isolated. For instance, it is known that circulating Endothelial Progenitor Cells (EPCs) originating from diabetic, obese, atherosclerotic, hypertensive, or smoking patients are less adhesive than those from healthy subjects, resulting in defective angiogenic and vasculogenic properties of these cells (Werner and Nickenig (2006) Arterioscler. Thromb. Vasc. Biol. 26:257-266; Werner and Nickenig (2006) J. Cell. Mol. Med. 10:318-332; Callaghan et al. (2005). Antioxid. Redox Signal 7:1476-1482; Loomans et al. (2005) Antioxid. Redox Signal 7:1468-1475; Roberts et al. (2005) J. Cell. Mol. Med. 9:583-591).

It has previously been proposed that treating EPCs preparations with growth factors prior to transplantation might enhance their pro-angiogenic effects. Thus, it has been shown that the adipose tissue-derived cytokine leptin could enhance significantly adhesion of EPCs to vitronectin-coated culture plates and to mature endothelial cells (Schroeter et al. (2006) 114:121). However, such a treatment has not been assessed in vivo.

As such, it is an object of the present invention to improve existing methods for preparing cells to be engrafted.

Blood coagulation, and arterial thrombosis in particular, involves platelet aggregation. An essential function of the aggregated platelets is to degranulate and release their contents into the blood stream. Platelet α-granules contain Thrombospondin-1 (TSP1), which forms up to 25% of released platelet proteins. TSP1 promotes enhanced platelet aggregation by participating in the formation of platelet-platelet, platelet-endothelial cell and platelet-extracellular matrix bridges, and further participates in inflammatory reactions involving monocytes-macrophages, lymphocytes, neutrophils, basophils, and even fibroblasts.

TSP1 was initially identified as a platelet released protein following thrombin activation. TSP1 can also be expressed in the vascular wall by smooth muscle cells after mechanical injury or during diabetes, and by endothelial cells during thrombosis, after perturbations of laminar blood flow, or consecutive to hypoxia.

TSP1 has a unique and complex structure with multiple domains, that activate a number of specific extracellular receptors. Different domains can thus sometimes induce apparently opposite signal pathways in the single cell type, as detailed below.

TSP1 interacts mainly with the scavenger receptor CD36 at the cell surface, as well as with Integrin-Associated Protein (CD47/IAP) and integrins.

TSP1 is mainly known as the archetypal endogenous anti-angiogenic factor. TSP1 plays an anti-angiogenic function in tumours and blocks their progression. TSP1 also inhibits re-endothelialisation following vascular injury and retinal neo-vascularisation in vivo.

The anti-angiogenic effects of TSP1 are mediated by at least one of its Type I domains and CD36 receptor activation. Indeed TSP1 binds CD36 through its CSVTCG sequence of its type I domains (Guo et al., (1997) Cancer Res, 57:1735-1742). In microvascular endothelial cells and in tumor endothelial cells, TSP1 binding to CD36 induces caspase activation, p38-MAPK and p59-Fyn kinase phosphorylation, resulting in apoptosis (Jimenez et al (2000) *Nature Medicine* 6:41-48). TSP1 is also known to trigger fibroblast apoptosis (Graf et al. (2002) *Apoptosis* 7:493-498), an additional cue as to how TSP1 may compromise tissue repair and vascularization.

Another well known TSP1 receptor is the quasi-ubiquitous Integrin-Associated Protein (CD47/IAP). TSP1 binding to CD47/IAP occurs through the carboxyterminus of TSP1 which notably comprises the sequence RFYVVMWK (4N1-1, SEQ ID NO: 3).

A peptide from the C-terminal domain of thrombospondin-1 known as 4N1-1 (Frazier (1993) *J. Biol. Chem.* 268: 8808-14) or its derivative 4N1K can bind to CD47/IAP in a similar manner as TSP1. This CD47/IAP-binding domain is highly conserved between species and TSP isoforms.

The activation of CD47 by TSP1 and 4N1-1 has been shown to induce the expression of CAM family proteins in mature endothelial cells. TSP1 thus enables the recruitment of circulating cells, in particular $\alpha_4\beta_1$ integrin-expressing inflammatory cells, towards the CAM-expressing vascular endothelium (Narizhneva et al. (2005) *FASEB J.* 19:1158-60).

However, such mechanisms have not been described in circulating undifferentiated progenitor cells, Furthermore, it has been shown that the activation of CD47 by TSP1 or 4N1-1 also induces apoptosis and the demise of mature endothelial cells (Freyberg et al. (2000) *Biochem Biophys Res Commun* 271:584-588; Freyberg et al. (2001) *Biochem Biophys Res Commun* 286:141-149; Graf et al. (2003) *Apoptosis* 8:531-538). CD47 agonists are thus known anti-angiogenic agents, that could be used in novel potential approaches to prevent the vascularization and growth of solid tumors (Manna et al. (2004) *Cancer Res* 64:1026-1036). CD47 expression and activation has also been linked to the inhibition of angiogenesis and endothelial death in models of angiogenesis in vivo (Isenberg et al. (2007) *Circ. Res.* 100:712-20).

It has further been proposed that TSP1 leads to the dismantlement of the intracellular skeleton and focal adhesion plaques, inhibition of proliferation, caspase activation, and eventually to apoptosis. Moreover, TSP1 inhibits Nitric Oxide (NO) signals, a powerful promoter of normal endothelial cell function and survival (Isenberg et al. (2006) *J. Biol. Chem.* 281:26069-80; Isenberg et al. (2007) *J. Biol. Chem.* 282:15404-15). Endothelial apoptosis thus appears to be a major aspect of the anti-angiogenic effects of TSP1.

In addition, TSP1 can be expressed by progenitor cells derived from diabetic bone marrow (Li et al (2006) *Circ Res* 98:697-704). In this case TSP1 was shown to block their adhesion and their contribution to vascular re-endothelialization after vascular injury, in keeping with its anti-angiogenic role in mature endothelial cells.

Accordingly, in view of prior studies, TSP1 and CD47 agonists do not seem to be usable to increase adherence of cells, and therefore to promote pro-angiogenic therapy or neo-vascularisation.

Besides, it is particularly interesting to note that systemic injection of significant doses of 4N1K peptide is not lethal and does not modulate gross coagulation parameters (Bonnefoy et al. (2006) *Blood* 107:955-64), despite its known prothrombotic effects on platelet aggregation (Voit et al. (2003) *FEBS Lett.* 544:240-5). It thus seems unlikely that 4N1-1, 4N1K or derived peptides have significant toxic effects in healthy subjects.

DESCRIPTION OF THE INVENTION

The present invention particularly arises from the unexpected finding, by the inventors, that cells liable to yield endothelial cells upon differentiation, treated by TSP1 or by TSP1 derivatives containing RFYVVMWK (SEQ ID NO: 3) had an increased ability to adhere to the extracellular matrix and to differentiate into endothelial cells, and that they could help restore a functional vasculature in ischemic tissues.

Thus, the present invention relates to an in vitro method for preparing progenitor cells having an increased adhesivity, wherein progenitor cells are contacted with an agonist of the CD47/IAP receptor thereby yielding progenitor cells presenting an increased adhesivity.

The present invention also relates to an in vitro method for preparing progenitor cells having an increased adhesivity, wherein progenitor cells are contacted with a polypeptide comprising or consisting of RFYVVMWK, or an analog of RFYVVMWK, thereby yielding progenitor cells presenting an increased adhesivity.

As intended herein, the expression "increased adhesitivity" means that progenitor cells prepared with the method according to the invention present a higher adhesion than non-treated progenitor cells. Higher adhesion can be determined by quantifying the number of adhesive progenitor cells on a test tissue or on a test substrate, such as gels of gelatine/vitronectin or fibrin.

It is particularly preferred that the prepared progenitor cells are intended for engraftment in a target tissue of an individual. Thus the present invention also relates to a method for preparing progenitor cells for engraftment in a target tissue of an individual, wherein the progenitor cells to be engrafted are contacted with an agonist of the CD47/IAP receptor or with a polypeptide comprising or consisting of RFYVVMWK, or an analog of RFYVVMWK, prior to engraftment.

As intended herein, the expression "engraftment" relates to the delivery and attachment or uptake of cells within a target tissue.

As intended herein, the expression "target tissue" relates to any group of cells, which cells have similar or different phenotypes, which exhibits one or several characteristics, as a whole, which makes it distinguishable from its environment. Target tissues as intended herein can be found in a multicellular organism, preferably an animal organism, more preferably a mammal organism, and most preferably a human organism. Preferably, the tissue is a non-liquid tissue. More preferably, the tissue is selected from the group constituted of cardiac and skeletal muscle, brain, pancreas, skin, kidney, blood vessels and other vascularized structures.

As intended herein, the expression "progenitor cells" relates to division-competent cells which are liable to differentiate in one or more cell types. Preferably, the progenitor cells are not differentiated. Progenitor cells encompass stem cells, in particular adult stem cells and embryonic stem cells.

As intended herein, the expression "progenitor cells known to be functional in cell therapy" relates to progenitor cells as defined above which display properties, such as an increased adhesivity, which are generally indicative of a subsequent successful attachment or uptake within a target tissue when delivered to an individual.

As intended herein, the expression "cell therapy" refers to the delivery of living cells in an individual in order to treat deficiencies, disorders or diseases.

As will be apparent to one of skill in the art, it is preferred that the progenitor cells to be prepared are eukaryotic cells. More preferably the progenitor cells are similar in type or are liable to yield, upon differentiation, cells similar in type, to cells which can be found in the target tissue. In particular it is preferred that the progenitor cells are liable to differentiate into endothelial cells, i.e. the progenitor cells are endothelial progenitor cells (EPC).

Preferably, the progenitor cells originate from tissues selected from the group constituted of adipose tissue, bone marrow, liver, spleen, and blood. As will be clear to anyone of skill in the art the progenitor cells can either be used in a purified form or in a non-purified form comprising other cells, which may notably originate from the same tissue as the progenitor cells. Unfractionated Bone Marrow Mononuclear Cells (BM-MNC) can be used as a non-purified form of progenitor cells, when the progenitor cells originate from bone marrow and are notably intended to restore blood vessels.

Preferably, the progenitor cells are of the same species than the individual. It is also particularly preferred that the progenitor cells originate from the individual.

Preferably also, progenitor cells to be used in the above-defined method express a CD47/IAP receptor.

As intended herein the expression "express a CD47/IAP receptor" means that the progenitor cells to be prepared comprise an mRNA which encodes the CD47/IAP receptor, or an RNA precursor thereof, and/or a protein consisting of the CD47/IAP receptor. Preferably, the mRNA comprises sequence SEQ ID NO: 1. Preferably also, the CD47/IAP receptor consists of sequence SEQ ID NO: 2. The detection of the mRNA, or of its precursors, can be carried out by various techniques well-known to one of skill in the art, such as RT-PCR for instance. The detection of the protein can also be carried out by various techniques well-known to one of skill in the art, such as immunodetection using anti-CD47/IAP antibodies for instance.

As intended herein, the expression "agonist of the CD47/IAP receptor" relates to any molecule which is liable to induce a response of the CD47/IAP receptor similar in nature to the response which is induced by binding of the TSP1 protein or the RFYVVMWK peptide (SEQ ID NO: 3). By way of example, agonists of CD47/IAP are liable to promote the expression and activation of $\alpha_2\beta_1$ integrins in vascular smooth muscle cells as described by Wang and Frazier (1998) *Mol. Biol. Cell* 9:865-874.

For instance, the agonist of the CD47/IAP receptor can be an anti-CD47 agonist antibody, such as the B6H12 antibody described by Gresham et al. (1989) *J. Cell. Biol.* 108:1935-1943; Wang and Frazier (1998) *Mol Cell Biol* 9:865-874; Ticchioni et al. *FASEB J* (2001) 15:341-350; and Barazi et al. (2002) *J Biol Chem* 277:42859-42866, the CIKm1 antibody, as described by Wilson et al. (1999) *J Immunol.* 163:3621-3628, or the 1F7 antibody, as described by Wang and Frazier (1998) *Mol Cell Biol* 9:865-874.

The agonist can also be the SIRPα1 protein as described by Jiang et al. (1999) *J Biol Chem* 274:559-562; Babic et al. (2000) *J Immunol* 164:3652-3658; Seiffert et al. (2001) *Blood* 97:2741-2749; and Liu et al. (2006) *J Mol Biol* 365:680-693.

However, it is preferred that the agonist is a polypeptide which comprises the amino acid sequence VVM.

Such agonists are well-known to the man skilled in the art.

In particular, they are selected from CD47/IAP receptor-binding peptides, such as those described in:

Voit et al. (2003) *FEBS Letters* 544:240-245; Barazi et al. (2002) *J Biol Chem* 277:42859-42866 (peptide 4N1-1 of sequence RFYVVMWK);

Gao et al. (1996) *J Cell Biol* 135:533-544; Wang et al. (1999) *J Cell Biol* 147:389-399; Kanda et al. (1999) *Exp Cell Res* 252:262-272; Ticchioni et al. (2001) *FASEB J* 15:341-350; Barazi et al. (2002) *J Biol Chem* 277:42859-42866; and Li et al. (2005) *J Immunol* 174:654-661 (peptide 4N1K of sequence KRFYVVMWKK, SEQ ID NO: 4);

Wilson et al. (1999) *J Immunol* 163:3621-3628; Barazi et al. (2002) *J Biol Chem* 277:42859-42866; and Isenberg et al (2006) *J Biol Chem* 281:26069-26080 (peptide 7N3 of sequence FIRYVVMYEGKK (SEQ ID NO: 9)); and U.S. Pat. No. 6,469,138 (RFYVVMWKQVTQS (SEQ ID NO: 10); and FIRVVMYEGKK (SEQ ID NO: 9)).

Preferably, the agonist is a polypeptide which comprises or consists in RFYVVMWK (4N1-1, SEQ ID NO: 3), such as KRFYVVMWKK (4N1K, SEQ ID NO: 4), or a derivative of RFYVVMWK.

4N1-1 notably represents amino acids 1034-1041 of human TSP1.

As intended herein, a derivative of RFYVVMWK, relates to any polypeptide derived from RFYVVMWK by insertion, deletion or insertion of at least one amino-acid and/or by chemical treatment, provided that the derivative presents essentially the same agonist properties than RFYVVMWK vis-à-vis the CD47/IAP receptor.

Preferably, the agonist is a fragment of the TSP1 protein. It is preferred that the TSP1 protein as intended herein is a human TSP1 protein, notably represented by GenBank reference NP-003237 and SEQ ID NO: 5, a mouse TSP1 protein, notably represented by GenBank reference AAA50611 and SEQ ID NO: 6, or a rat TSP1 protein, notably represented by GenBank reference NP-0001013080 and SEQ ID NO: 7. Most preferably, the TSP1 protein is a human TSP1. In particular, as will be apparent to the man skilled in the art, any fragment of the TSP1 protein which comprises RFYVVMWK can be considered as an agonist of the CD47/IAP receptor as intended herein.

Preferably, when the agonist is a fragment of the TSP1 protein, it does not comprise type I repeats, nor CD36-agonist domains, such as the sequence CSVTCG (SEQ ID NO: 8).

As intended herein an "analog" of the RFYVVMWK peptide relates to any molecule which is similar in shape, charge repartition and hydrophilicity/hydrophobicity repartition to peptide RFYVVMWK.

In another advantageous embodiment of the above-defined method, the prepared progenitor cells are liable to differentiate into mature cells in the target tissue and differentiation of the prepared cells is accelerated compared to similar cells which have not been prepared according to said method.

In a further embodiment of the above-defined method, the cells are preferably contacted with the agonist for 10 seconds to 2 hours.

In another embodiment, the above method comprises a step of further selecting adherent cells among prepared cells, for instance onto gels of gelatin/vitronectin or fibrin.

Indeed different cells may respond differently to the agonist contacting phase, thus separating cells into adherent and less-adherent fractions, and using the fraction with enhanced adhesion capacity is advantageous to improve rates of therapeutic cell engraftment.

The present invention also relates to the use of cells prepared by the in vitro method as defined above, for the manufacture of a medicament intended for treating an individual in need of cell engraftment, or to a method for treating an individual in need of cell engraftment, wherein a therapeutically effective amount of cells prepared by the in vitro method as defined above is administered to said individual. It also relates to cells prepared by the in vitro method as defined above for treating an individual in need of cell engraftment.

The present invention further relates to the use of at least one of the above-defined agonist of the CD47/IAP receptor, preferably in association with cells prepared by the above-defined in vitro method, for the manufacture of a medicament intended for treating an individual suffering from an insufficiency of the vascular system, or to a method for treating an individual suffering from an insufficiency of the vascular system, wherein a therapeutically effective amount of at least one of the above-defined agonists of the CD47/IAP receptor, preferably in association with cells prepared by the above-defined in vitro method, is administered to said individual. It also relates to the above defined agonists of the CD47/IAP receptor, preferably in association with cells prepared by the above-defined in vitro method, for treating an individual suffering from an insufficiency of the vascular system.

The present invention also relates to the use of at least one of the above-defined polypeptides comprising or consisting of RFYVVMWK, or of an analog of RFYVVMWK, preferably in association with cells prepared by the above-defined in vitro method, for the manufacture of a medicament intended for treating an individual suffering from an insufficiency of the vascular system, or to a method for treating an individual suffering from an insufficiency of the vascular system, wherein a therapeutically effective amount of at least one of the above-defined polypeptides comprising or consisting of RFYVVMWK, or of an analog of RFYVVMWK, preferably in association with cells prepared by the above-defined in vitro method, is administered to said individual. It also relates to the above-defined polypeptides comprising or consisting of RFYVVMWK, or of an analog of RFYVVMWK, preferably in association with cells prepared by the above-defined in vitro method, for treating an individual suffering from an insufficiency of the vascular system.

As intended herein the individual preferably relates to an animal, more preferably to a mammal, and most preferably to a human.

Preferably, the individual suffers from an insufficiency of the vascular system. More preferably, the individual is in need of blood vessel reconstruction or neoformation. Most preferably, the individual suffers from a pathology selected from the group constituted of atherosclerosis, diabetes, obesity, myocardial infarction, coronaropathy, diabetic retinopathy, nephroangiosclerosis, cerebral ischemia, thrombosis, endothelial dysfunction, pulmonary hypertension, traumatic cutaneous wounds, ulcers, and burns.

The present invention also relates to an in vitro method for determining if an individual as defined above would benefit from the treatment with progenitor cells known to be functional in cell therapy as defined above, wherein
(i) progenitor cells as defined above, preferably of the same type as that of the progenitor cells known to be functional in cell therapy, taken from the individual, are contacted with an agonist of the CD47/IAP receptor as defined above or with a polypeptide comprising or consisting of RFYVVMWK, or an analog of RFYVVMWK, as defined above;
(ii) the adhesivity of the contacted progenitor cells is assessed; whereby if the progenitor cells present an increased adhesivity, it is determined that the patient is likely to benefit from the treatment with said progenitor cells known to be functional in cell therapy.

The present invention also relates to an in vitro method for determining if an individual as defined above would benefit from the treatment with cells prepared by the in vitro method for preparing progenitor cells having increased adhesivity as defined above, wherein:
(i) progenitor cells as defined above, taken from the individual, are contacted with an agonist of the CD47/IAP receptor as defined above or with a polypeptide comprising or consisting of RFYVVMWK, or an analog of RFYVVMWK, as defined above;
(ii) the adhesivity of the contacted progenitor cells is assessed;

whereby if the progenitor cells present an increased adhesivity, it is determined that the patient is likely to benefit from the treatment with cells prepared by the in vitro method for preparing progenitor cells having increased adhesivity as defined above.

Conversely, the present inventors have shown that in mice knocked out for wild type TSP1 expression, cells liable to yield endothelial cells upon differentiation presented a decreased ability to be recruited towards sites of thrombosis. Furthermore, platelet degranulation products released by TSP1-deficient platelets isolated from these animals showed reduced ability to stimulate the adhesion of cells liable to yield endothelial cells upon differentiation to immobilized extracellular matrix in vitro.

As such, the present invention further relates to a method for preventing cell adhesion or cell engraftment in an individual presenting pathological processes implying cell adhesion or cell engraftment, wherein an effective amount of at least one antagonist of the CD47/IAP receptor is administered to said individual.

The present invention also relates to the use of at least one antagonist of the CD47/IAP receptor, for the manufacture of a medicament intended for preventing cell adhesion or cell engraftment in an individual presenting pathological processes implying cell adhesion or cell engraftment. It also relates to an antagonist of the CD47/IAP receptor for preventing cell adhesion or cell engraftment in an individual presenting pathological processes implying cell adhesion or cell engraftment.

As intended herein, the expression "antagonist of the CD47/IAP receptor" relates to any compound liable to inhibit the activation of the CD47/IAP receptor and/or to inactivate the CD47/IAP receptor, but also to any compound liable to inhibit binding of TSP1, and also to any compound liable to inhibit binding of RFYVVMWK sequence-containing agonists or any RFYVVMWK sequence-mimicking agonists to their cognate receptors, such as, in particular the CD47/IAP receptor.

Preferably, the pathological processes are diabetic retinopathy and atherosclerosis.

Such a use or method might be useful, particularly in the frame of cell therapy, to prevent the undesirable adhesion or engraftment of administered therapeutic cells into non-targeted tissues and/or at unwanted sites. In this particular case, the CD47/IAP receptor antagonist might be administered locally at sites where the adhesion of progenitor cells is to be prevented.

EXAMPLES

Materials and Methods

Reagents and Antibodies

Figure 1:
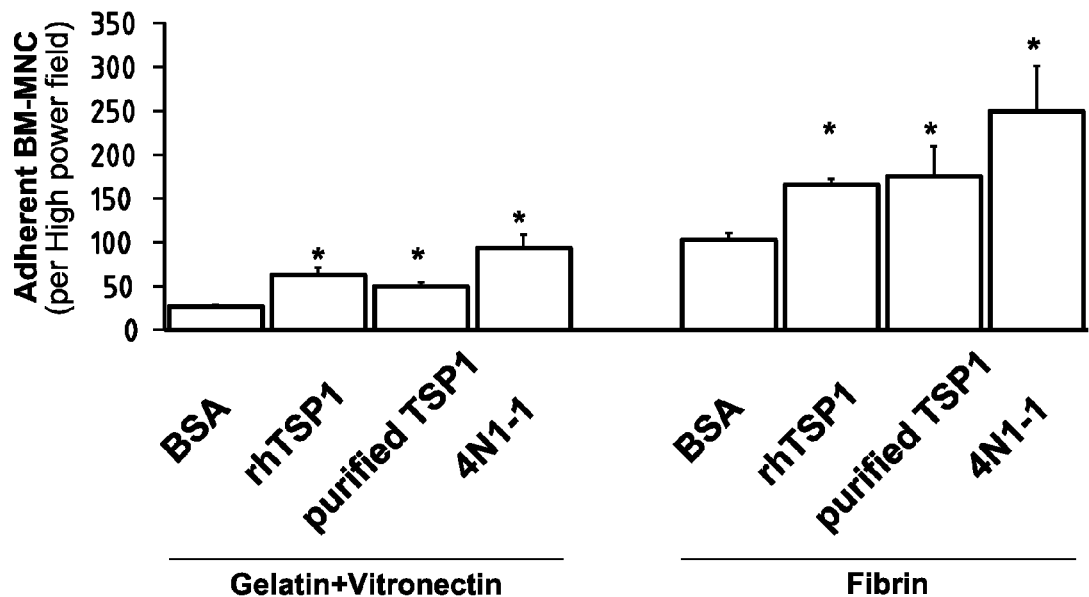
FIG. 1 represents adhesion of PBMC for 30 min onto gelatin-vitronectin or fibrin gels after pre-treatment for 2 hours with BSA, or recombinant or purified TSP1, or peptide 4N1-1. (*p<0.05 vs BSA).

Human recombinant TSP1 was produced by EMP-Genetech and Human purified TSP1 was prepared by Dr. Arnaud Bonnefoy at Inserm Unit U553 at Hôpital S$^r$ Louis (Paris). Synthetic peptides 4N1-1 (RFYVVMWK, SEQ ID NO: 3) and 4N1-2 (RFYVVM, SEQ ID NO: 11) were obtained from Bachem Ltd. Peptides 7N3 (FIRVVMY- EGKK, SEQ ID NO: 9), mutated 4N1-1 called 4NGG (RFYGGMWK, SEQ ID NO:12), and mutated 7N3 called 7NGG (FIRGGMYEGKK, SEQ ID NO:13) were synthesized by NeoMPS, France. Purified Human fibronectin and thrombin, staurosporine and bovine serum albumin (BSA) were obtained from Sigma, fibrinogen from American Diagnostica.

For fluorescence labelling and inhibition of cell surface receptors, mouse monoclonal anti-human CD47 IgG1 (clone B6H12) and FITC-conjugated anti-mouse integrin $\beta_1$ harmenian hamster IgG were purchased from Santa Cruz. Control isotype mouse IgG1 matched with B6H12 was provided by Chemicon. Biotin-conjugated anti-mouse integrin $\beta_2$ rat IgG2akappa, phycoerythrin-conjugated anti-mouse PSGL1 rat IgG1kappa, FITC-conjugated harmenian hamster IgG, biotin-conjugated rat IgG2a-kappa, phycoerythrin-conjugated rat IgG1kappa and Per-CP-conjugated streptavidin were purchased from BD Pharmingen. Phycoerythrin-conjugated anti-mouse integrin $\beta_3$ harmenian hamster IgG, biotin-conjugated anti-mouse integrin $\alpha_v$ rat IgG1kappa, phycoerythrin-conjugated harmenian hamster IgG and biotin-conjugated rat IgG1kappa were provided by eBiosciences. Analysis was performed with a Canto-II fluorescence-assisted cell sorter (FACS) from Becton-Dikinson.

Recombinant human stroma-derived factor 1α (SDF1) was purchased from Calbiochem, recombinant chimeric ephrin-B2-Fc (EphB2-Fc) was obtained from R&D Systems, and recombinant human leptin was provided by Biovision.

Animals 10 week-old wild type male mice on C57Bl/6 and Swiss genetic backgrounds (Charles River) were used. Male TSP1-deficient Swiss mice were obtained from Dr. Arnaud Bonnefoy at Inserm Unit U553 at Hôpital S$^t$ Louis (Paris, France). For intra-vital microscopy, mice were used at 4 weeks of age. Obese Ob/Ob leptin-deficient transgenic mice on C57bl6 background were obtained from Harlan-France. Type 1 diabetes (insulin-dependent) was induced in C57bl6 male mice by injecting streptozotocine (which is known to destroy beta cells of the pancreas) every day for 1 to 2 weeks and until the glycemia reaches 300 mg/kg. The mice are then considered diabetic and kept for 2 months on standard chow diet.

Cell Culture

Tibias, femurs and humerus of C57BL/6 male mice were carefully dissected, bone marrow was extracted and dissociated, and bone marrow mononuclear cells (BM-MNC) were separated by differential centrifugation on Ficoll gradients (Histopaque-1083, Sigma), (2,000 r.p.m, 25 min). BM-MNC were then washed with PBS and pelleted (2,000 r.p.m, 10 min).

For FACS assays, fresh cells were treated with the indicated peptides and times, fixed with 4% paraformaldehyde in PBS, and analyzed with a Beckman-Coulter Epics-XL cell sorter to determine cell size distribution by analysis of forward and side scatter. Data were presented either as dot distribution diagrams, or as individual FSc and SSc distribution profiles.

Alternatively, BM-MNC were resuspended and cultured in endothelial basal growth medium (EBM; Clonetics), or EBM2 (Clonetics) enriched in vascular endothelial growth factor-165 (VEGF) and fibroblast growth factor-2 (FGF2), and further supplemented with fetal calf serum (FCS, 20%). Cells were cultured in wells pre-coated with gelatine (0.1%)—vitronectin (0.5 μg/ml; Sigma). After culture in the indicated conditions of peptide concentration and time, cell spreading was measured with the ImageJ image analysis software by delimiting the individual cells to determine the area they occupied. Over 50 cells were measured in 3 randomly selected fields (×400 magnification) for 3 independent cell cultures. Spreading was expressed in relative area units per cell.

Circulating mouse blood was obtained via venipuncture in the retro-orbital sinus, and mixed with anticoagulant buffer containing heparin (5 UI/ml). Circulating peripheral blood mononuclear cells (PBMC) were purified through Ficoll gradient centrifugation (Histopaque-1083, Sigma), (2,000 r.p.m, 25 min). Cells were washed and pelleted (2,000 r.p.m, 5 min) twice in PBS to eliminate contaminating platelets.

SV40-transformed mouse lymph node endothelial cells (SVEC from ATCC), were grown in Dulbecco's Modified Eagle Medium (DMEM) supplemented with 20% FCS in 24 well plaques until they reached full confluency (7 days). SVEC monolayers were activated with 5 nM murine interleukin-1β (Calbiochem) for 2 h prior to cell-cell adhesion experiments.

Human umbilical cord blood (30-50 ml) was collected in sterile tubes containing heparin (15 UI/ml, Sanofi) following standard protocols in agreement with Hôpital Lariboisiére and Inserm ethical guidelines. PBMC were isolated via Ficoll gradient centrifugation (Histopaque-1077, Dominique Dutscher). To eliminate mature endothelial cells, mononuclear cells were seeded ($6.10^6$ cells/ml) in culture dishes (100×20 mm) at 37° C. with 5% $CO_2$ for 16 h. Adherent cells were eliminated. Non-adherent cells were cultured and differentiated into Human umbilical cord blood-derived endothelial progenitor cells (HUCB-EPC) in 6-well plates ($10^7$ cells/well) on collagen type 1 matrix (Coll1; 90 μg/ml, Sigma) in M199 growth medium (Gibco) complete with L-glutamine, HEPES buffer (25 mM; Eurobio), antibiotics and antimycotics (penicillin 10000 units/ml, streptomycin 10,000 μg/ml, fongizone 25 μg/ml) and 20% FCS (Dominique Dutscher), as well as 10 ng/ml VEGF (R&D Systems).

Pretreatment of Cell Preparations

To evaluate the effects of TSP1 or peptides derived from its carboxyterminal sequence, 4N1-1 and 4N1-2, on cell adhesion onto gelatin/vitronectin, fibrin gels or activated SVEC monolayers, $2.10^6$/ml BM-MNC or PBMC, or $10^6$/ml HUCB-EPC were pretreated for 2 h at 37° C. in an incubator with 5% $CO_2$, in the presence of TSP1 (50 to 100 μM), or the 4N1-1 or 4N1-2 peptides (100 μM), or control BSA (1%), or with mouse monoclonal anti-human CD47 IgG1 B6H12 (40 μg/ml), or matched control isotype mouse IgG1 (40 μg/ml), before PBS washes and culture for the specified length of time. For adhesion experiments, supernatants were removed, adherent cells were gently washed with PBS. The number of adherent cells per high power field was counted in 3 to 5 fields per well using an inverted phase-contrast microscope at high magnification (×400).

Platelet-Poor Plasma

Mouse circulating blood was obtained through retro-orbital sinus puncture and mixed with anti-coagulant buffer containing heparin (5 UI/ml), and centrifuged for 15 min at 2,000 r.p.m to eliminate red blood cells and leukocytes. The supernatant was collected and centrifuged for 5 min at 11,000 r.p.m to eliminate platelets. This final supernatant was considered as platelet-poor plasma (PPP).

Platelet Degranulation Products

Mouse blood was obtained via intra-cardiac puncture after terminal anesthesia through Pentobarbital-Na overdose (Cerval, France). Blood was anti-coagulated with ACD-C buffer (citric acid 130 mM, trisodic citrate 124 mM, glucose 110 mM) and incubated with prostaglandin E1 (PGE1 10-8 M) for 1 h at room temperature to preclude spontaneous platelet activation. Blood was then centrifuged for 15 min at 120 g at 15° C. to collect platelet-rich plasma (PRP). PRP was then mixed with wash buffer (NaCl 140 mM, KCl 5 mM, trisodic citrate 12 mM, glucose 10 mM, sucrose 12.5 mM, pH 6.0), and centrifuged for 15 min at 1,200 g. The platelets pellet was washed and pelleted again for 15 min at 1,200 g, before the platelets were re-suspended in reaction buffer (HEPES 10 mM, NaCl 140 mM, KCl 3 mM, $MgCl_2$ 0.5 mM, $NaHCO_3$ 5 mM, glucose 10 mM, pH 7.4). Platelets were numerated, the suspension was adjusted to 600,000 platelets/μl and left at room temperature for 30 min to eliminate PGE1 prior to functional aggregation studies.

Platelet aggregation was measured with a Chronolog aggregometer (Kordia, Holland) following the turbidity method by Born (1962). Platelet suspension (400 μl) was incubated at 37° C. for 5 min and inserted into the aggregometer with stirring. 0% optical transmission was calibrated with the platelet suspension, 100% transmission was set with buffer alone. Optical transmission recording was initiated after addition of calcium and other agonists such as Thrombin Receptor Activating Peptide-6 (TRAP, 100 μM) and adenosine diphosphate (ADP 10 μM). After 5 min of aggregation-degranulation, platelets were pelleted with a 15 second pulsed centrifugation and eliminated. The supernatant contained the platelet degranulation products (PDP).

Bone Marrow-Derived EPC Labelling

BM-MNC were cultured onto gelatin/vitronectin in EBM medium for 5 days. After eliminating non adherent cells, EPC were identified through double-labelling for two endothelial characteristics: incorporation of Dil-labelled acetylated low density lipoproteins (Dil-Ac-LDL; 1 μg/ml, BioHarbor Products; red fluorescence) and binding of FITC-labelled BS1-lectin (1 μg/ml, Sigma; green fluorescence). Double fluorescence allowed the microscopic identification and counting of EPC in 3 to 5 fields per well (400× magnification). Experiments were repeated at least three times, and results expressed as percentages of EPC.

Integrin and PSGL1 Cell Surface Expression

To determine cell surface protein expression, BM-MNC were blocked with PBS-BSA 5% for 30 min before incubation with FITC-conjugated anti-integrin $β_1$, biotin-conjugated anti-integrin $β_2$, PE-conjugated anti-integrin $β_3$, biotin-conjugated anti-integrin $α_v$, PE-conjugated anti-PSGL1 antibodies or their matched control isotype IgG (all 0.5 mg/l) for 45 min in PBS-BSA 2%. BM-MNC were pelleted (5 min, 2,000 r.p.m) and resuspended with PBS-BSA 2%. Percentages of labelled cells were determined by flow cytometry with an Canto-II cell sorter (Becton-Dikinson). Percentages of non-immune isotypic control antibody-labelled cells were compensated for.

Apoptosis Evaluation Via Observation of Nuclear Morphology

BM-MNC were grown onto gelatin/vitronectin matrix for 5 days in EBM in the continued presence of TSP1 or the 4N1-1 and 4N1-2 peptides, or treated for the last 24 h only. Staurosporine (2 μg/ml, 6 h) was used as a positive control for apoptosis induction. Non adherent cells were eliminated and adherent cells fixed with PBS-PFA 4% followed by addition of DAPI (Di-aminidophenylindol, 0.01 mg/ml) that becomes fluorescent after integration between DNA bases. Nuclear morphology was analyzed by fluorescence microscopy and percentages of apoptotic nuclei that displayed fragmentation or chromatin condensation were calculated in 3 to 5 fields per well (400× magnification). Experiments were repeated at least three times.

Apoptosis Evaluation Via Quantification of Intact DNA Content

BM-MNC were isolated and treated with 4N1-1 peptide for 10 or 120 min, washed with PBS and cultured in EBM onto gelatin/vitronectin matrix for up to 24 hours. Untreated fresh cells served as control for live cells. As a positive control for apoptosis, cells in suspension were treated with staurosporine (2 μg/ml, 6 h). After treatment and culture, non adherent and adherent cells were harvested and analyzed separately, fixed with ice-cold ethanol 70% in PBS, and incubated for 45 min in PBS containing Triton X-100 (0.05%), propidium iodide (PI; 50 μg/ml) and RNase-A (100 μg/ml). PI becomes fluorescent after integration between DNA bases. DNA content was then analyzed by fluorescence-assisted cell sorting (FACS; Beckman-Coulter) and percentages of apoptotic nuclei that displayed DNA fragmentation and reduced fluorescence were measured. Experiments were repeated three times.

Time-Dependent Recruitment of BM-MNC in Experimental Thrombosis

The inventors adapted an experimental model of arterial thrombosis by Kurz et al. (1990) Thromb Res 60:269-280 and used iron chloride ($FeCl_3$) as a chemical inducer. Wild type C57bl6, Swiss, or TSP1-deficient Swiss mice were laparotomized after terminal anaesthesia with pentobarbital and local cutaneous application of xylocaïne 5% as an additive analgesic. BM-MNC were pre-treated for 2 h with the fluorescent dye 'Cell Tracker-Orange' (5 μM; Molecular Probes), and the synthetic peptides 4N1-1 or 4N1-2 (100 μM), or control BSA (1%). BM-MNC were washed with PBS and administered into the circulation through the retro-orbital sinus ($2.10^6$ cells/100 μl/animal). Mesenteric artery-vein pairs were dissected free and exposed for real time intra-vital microscopy. Prepared whole mice were placed on the stage of an inverted fluorescence microscope (Ellipse TE300) fitted with an analogic camera (LHESA Electronic, 40 images/sec) connected to a VHS recorder, or in line with a high resolution numeric camera (DXM1200, Nikon) linked to the Act-1 image acquisition software (Nikon). Basal BM-MNC recruitment onto the intact vascular wall of a selected venule was recorded for 2 min. A piece (1-2 $mm^3$) of agar gel (1%) containing $FeCl_3$ (500 mM) was then applied locally to induce progressive vascular thrombosis through diffusion. BM-MNC recruitment on the thrombosed vascular surface was recorded for a further 15 min. Recordings were analyzed and the number of new BM-MNC/vascular wall interactions was calculated per minute, every minute. Firm adhesions (adherent cells static for over 30 sec) were counted and accumulated over the first 10 minutes after thrombosis induction. The average rolling speed of BM-MNC interacting with the vascular wall was calculated per cell over the first 10 minutes after thrombosis induction by measuring the distance traveled over time on a calibrated screen, and conversion into μm/sec.

Pro-Angiogenic Effects of BM-MNC During Experimental Hindlimb Ischemia

Anaesthetized mice (m=8 to 10 animals/group) underwent arterial ligation at the proximal origin of the right deep femoral artery to induce hindlimb ischemia. All mouse manipulations were performed following the ethical rules and guidelines of our institutions. Ligated mice were injected with BM-MNC prepared as indicated above. After 14 days of ischemia, hindlimb neovascularization was studied using two independent methods: vascular density was evaluated through high resolution microangiography. Anaesthetized animals were injected with barium sulphate as a contrast agent through a catheter connected to a syringe inserted in the abdominal aorta, under the control of a calibrated pump. This system allowed the continued monitoring of a constant injection flow. Images of the hindlimb vascular system were acquired via X-ray micro-angiography. Angiographic scores were determined by quantifying image pixels occupied by blood vessels and expressed as percentages. Changes in cutaneous flow were analyzed by Laser Doppler coupled to an image analysis software. Variations in illumination and room temperature were taken into account by expressing hindlimb perfusion as a ratio of values obtained in the ischemic right limb divided by those of the non-ischemic control left limb.

Statistical Analysis

All experiments were repeated at least three times. For in vitro experiments, statistical analysis was performed with the Student T-test. Neovascularization results were analyzed with the ANOVA test, and inter-group comparisons (m=5 to 10 animals/group) were performed with the Mann-Whitney test. Significance was achieved when $p<0.05$.

Example 1

Effects of Platelet Proteins on Mouse BM-MNC, Mouse PBMC and Human HUCB-EPC Adhesion Mouse BM-MNC and HUCB-EPC adhesion was evaluated in vitro. The effects of purified or recombinant platelet proteins, or peptide agonists of the CD47/IAP receptor was characterized. Two main approaches were used:
1. Pre-incubation of the cells with platelet proteins for 2 h before measuring their adhesion on gelatin/vitronectin control matrix or fibrin gels for 30 min.
2. Cell adhesion on gelatin/vitronectin control matrix or fibrin gels for 16 h in the presence of platelet proteins in solution.

Figure 2:
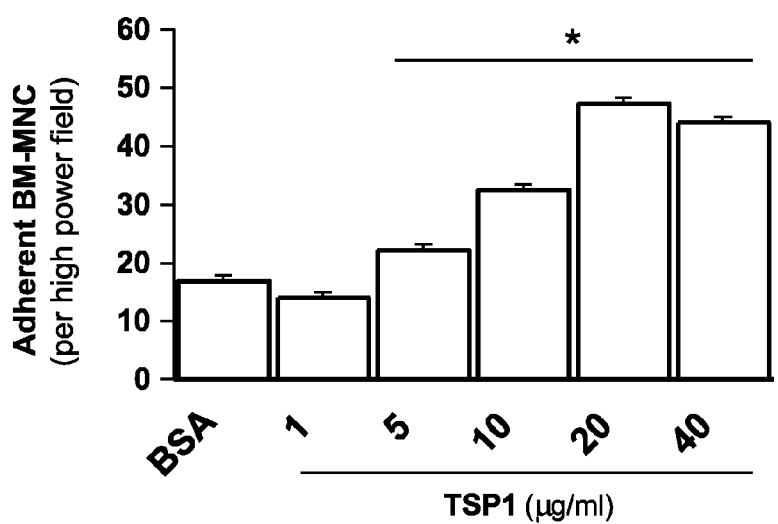
FIG. 2 represents adhesion of BM-MNC for 30 min onto gelatin-vitronectin after pre-treatment for 2 hours with increasing concentrations of recombinant TSP1 (* p<0.05 vs BSA)
Figure 5:
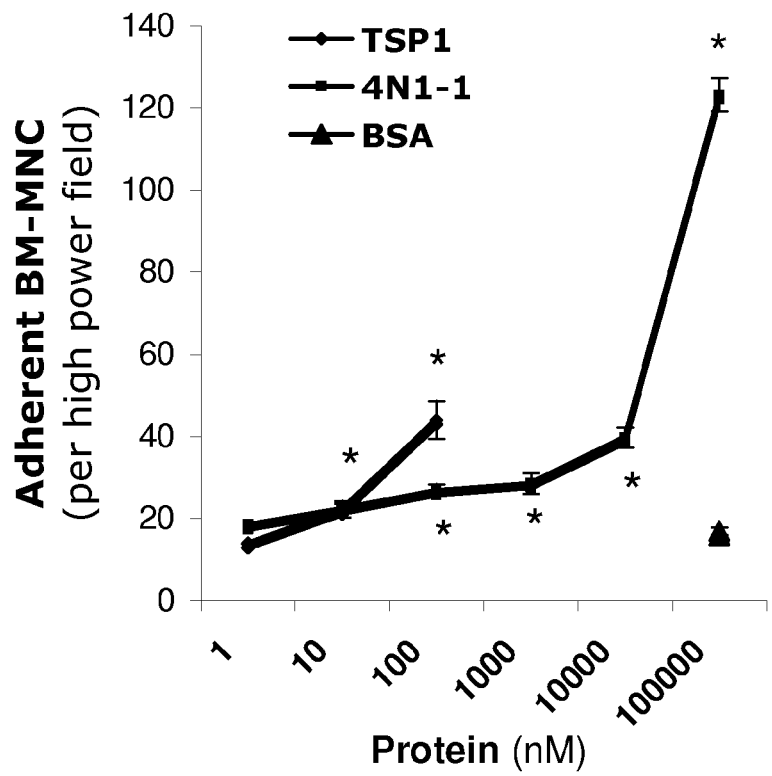
FIG. 5 represents a comparative study of the adhesion of BM-MNC for 30 min onto gelatin-vitronectin after pre-treatment for 2 hours with BSA, or increasing concentrations of recombinant TSP1, or increasing concentrations of peptide 4N1-1. (* p<0.05 vs BSA).
Figure 6:
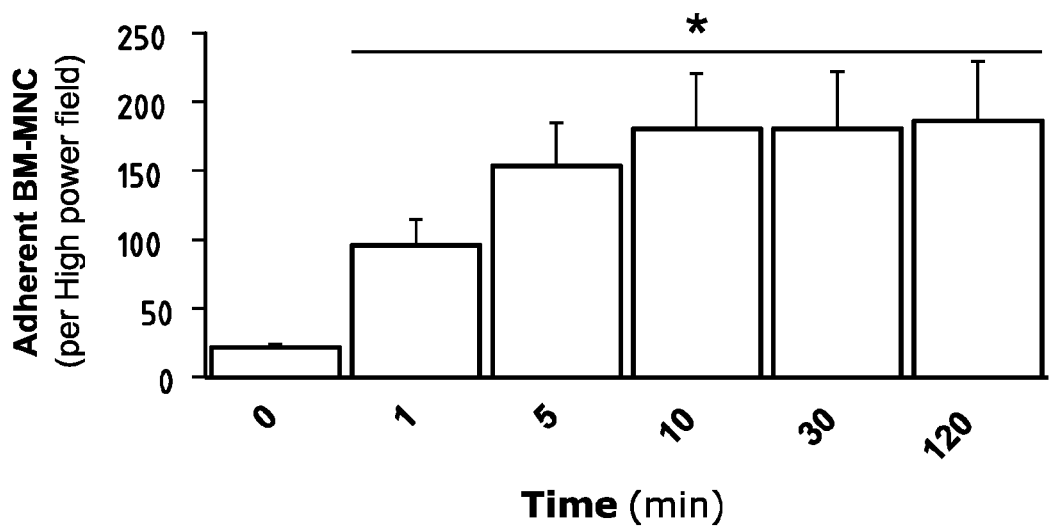
FIG. 6 represents the adhesion of BM-MNC onto gelatin-vitronectin for 30 min, after pre-treating BM-MNC with peptide 4N1-1 (50 mM) for 0, 1, 5, 10, 30 or 120 min. (*p<0.05 vs BSA).

Effects of Pre-Incubatinq BM-MNC with TSP1, or Peptide 4N1-1 on their Adhesion onto Gelatin/Vitronectin or Fibrin Gels:

BM-MNC were pre-treated with recombinant or purified TSP1 or peptide 4N1-1 for 2 h, and their adhesion onto gelatin/vitronectin matrix or fibrin gels was measured for 30 min. Pre-treatments with TSP1, and particularly with the 4N1-1 peptide strongly stimulated adhesion onto gelatin/vitronectin (+160.6%, $p<0.05$; and +249.6%, $p<0.05$, respectively), and on fibrin (+74.0%, $p<0.05$; and +186.0%, $p<0.05$, respectively), compared with BSA (FIG. 1). BM-MNC were pre-treated with increasing concentrations of recombinant TSP1 from 1 to 40 mg/ml for 2 h, and their adhesion onto gelatin/vitronectin was measured after 30 min. TSP1 stimulated BM-MNC adhesion significantly onto gelatin/vitronectin from 5 µg/ml up. Maximal stimulation was reached at 20 µg/ml (+179.3%, $p<0.05$), compared with BSA (FIG. 2). Stimulation with 4N1-1 peptide was relatively more potent onto gelatin/vitronectin than fibrin gels, and was dose-dependent from 100 nM (FIG. 5). 100 µM of 4N1-1 peptide stimulated adhesion about 6 times more effectively than the most efficient tested dose of TSP1 (100 nM). 4N1-1 peptide stimulation of BM-MNC adhesion was complete and produced near-maximal effects after only a 5 to 30 minute pre-incubation (FIG. 6). The increased capacity of the cells to adhere was maintained for at least 2 hours after initiating of the stimulation.

Figure 4:
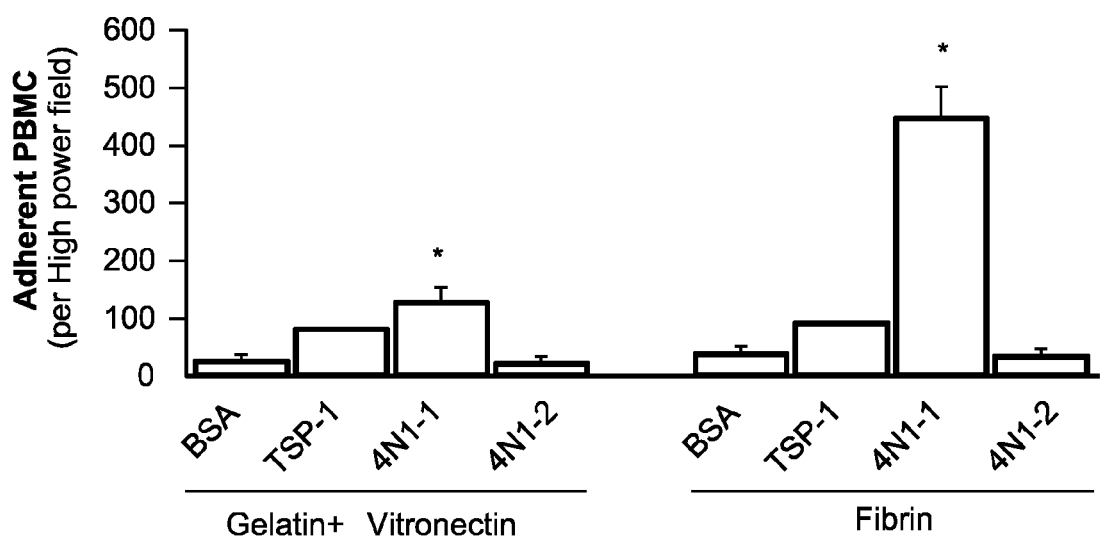
FIG. 4 represents adhesion of PBMC for 30 min onto gelatin-vitronectin or fibrin gels after pre-treatment for 2 hours with BSA, or recombinant or purified TSP1, or peptides 4N1-1 and 4N1-2. (* p<0.05 vs BSA).

Effects of Pre-Incubating PBMC with TSP1, or Peptide 4N1-1 on their Adhesion onto Gelatin/Vitronectin or Fibrin Gels:

Pre-incubation of PBMC with the 4N1-1 peptide induced similar effects as in BM-MNC and stimulated their adhesion onto gelatin-vitronectin (+403.2%, $p<0.05$), and even more onto fibrin gels (+1, 107.8%, $p<0.05$), (FIG. 4).

Figure 3:
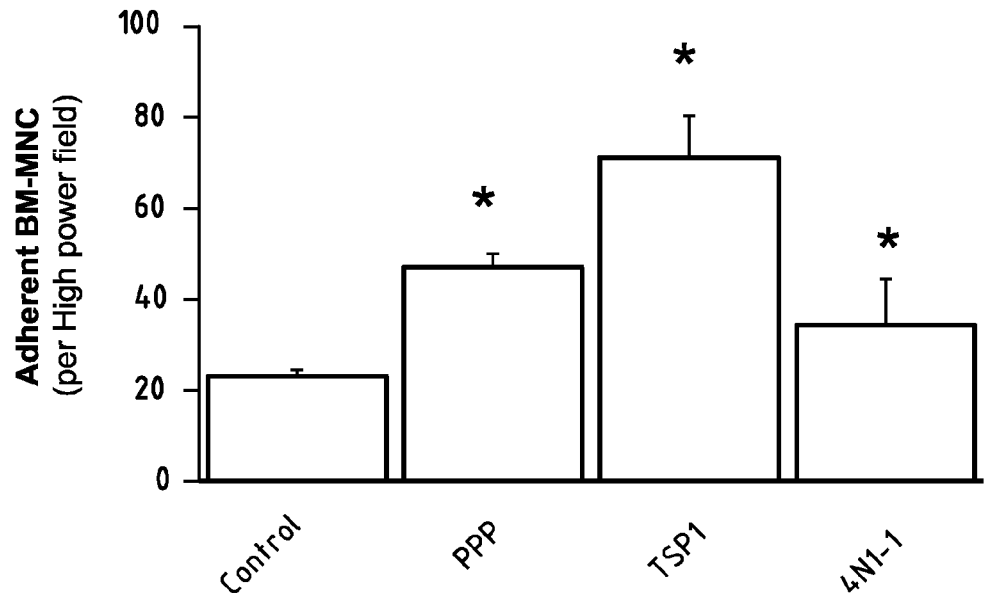
FIG. 3 represents adhesion of BM-MNC onto gelatin/vitronectin for 16 h in the absence or presence of PPP, recombinant TSP1, or peptide 4N1-1. (* p<0.05 vs Gel.+Vit.)

Effects of TSP1, 4N1-1 Peptide and PPP in Solution on BM-MNC Adhesion onto Gelatin/Vitronectin for 16 h:

BM-MNC were incubated for 16 h on gelatin/vitronectin matrix in the presence of PPP, recombinant TSP1 (100 µg/ml), or peptide 4N1-1 (100 µM) before adhesion was quantified through direct cell counts by phase-contrast microscopy. As reported in FIG. 3, TSP1 stimulated adhesion by over three fold compared to the gelatin/vitronectin control (+206.8%, $p<0.05$). Synthetic peptides 4N1-1 also increased adhesion significantly over 16 h, although less efficiently than with a 2 h pre-incubation.

Figure 7:
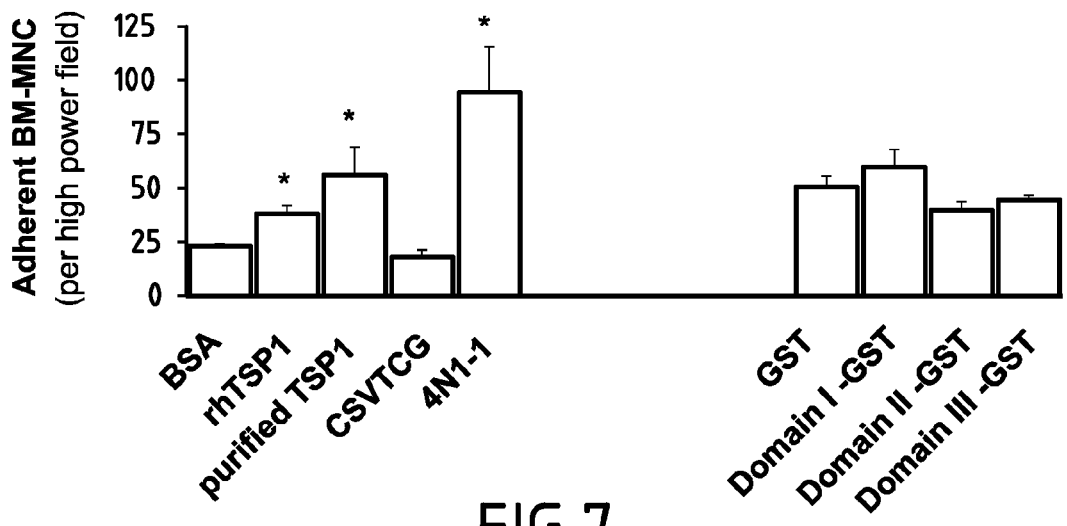
FIG. 7 represents BM-MNC adhesion onto gelatin-vitronectin for 30 min after pre-treatment for 2 hours with recombinant or purified TSP1, or peptides CSVTCG, 4N1-1, or BSA as control (left panel; * p<0.05 vs BSA), or with GST-coupled recombinant domains NH2, type I, type II, or type III of Human TSP1, or the GST tag alone (right panel).

Effects of Pre-Incubating BM-MNC with Human Recombinant or Purified TSP1, or with the Peptides CSVTCG, 4N1-1, or with Various Recombinant Domains of TSP1, on their Adhesion onto Gelatin/Vitronectin:

BM-MNC were then pre-treated for 2 h with BSA (control), human recombinant or purified TSP1, or peptides CSVTCG, 4N1-1, or with the peptide GST alone or coupled to the recombinant domains NH2, I, II, and III of human TSP1, and their adhesion onto gelatin/vitronectin was measured after 30 min. As shown in FIG. 7, peptide 4N1-1 stimulated BM-MNC adhesion particularly strongly compared with BSA (+310.4%, $p<0.05$). Recombinant and purified TSP1 also stimulated adhesion significantly (+65.6, and +143.8%, $p<0.05$, respectively). There was no significant difference between their respective effects (p=0.058). None of the tested recombinant GST-coupled TSP1 domains had any effects compared to control GST alone. On the other hand, a 21% inhibition of adhesion with the peptide CSVTCG, compared with BSA ($p<0.05$) was noted.

Figure 26:
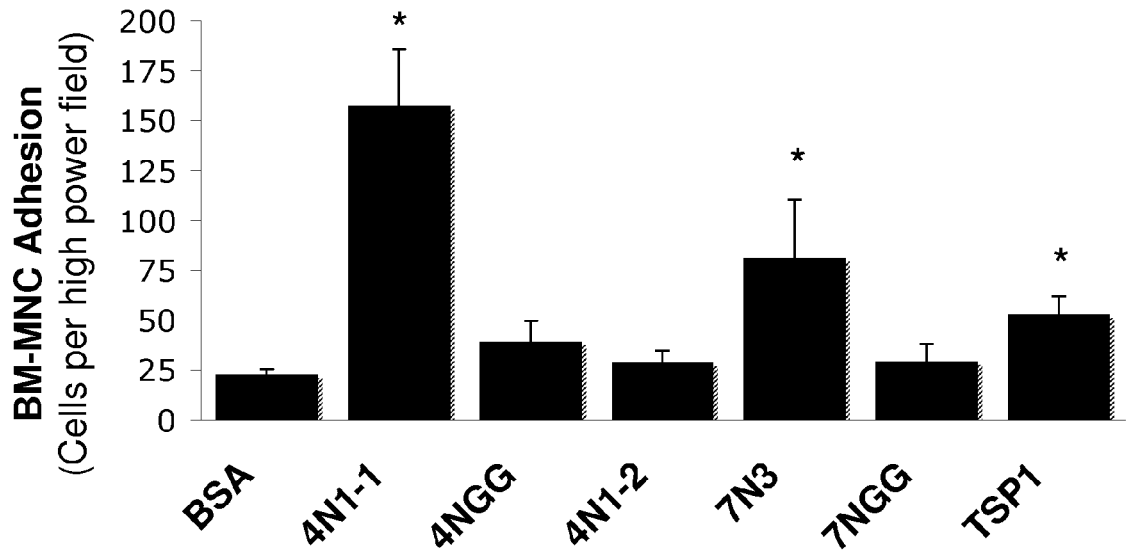
FIG. 26 represents BM-MNC adhesion onto gelatin-vitronectin for 30 min after pre-treatment for 2 hours with peptides 4N1-1, 4NGG, 4N1-2, 7N3, 7NGG, or recombinant TSP1, or BSA as control (* p<0.05 vs BSA).

Alternatively, BM-MNC were then pre-treated for 2 h with BSA (control), human recombinant or purified TSP1, or peptides 4N1-1, 7N3, and 4N1-2, or with the mutated sequence 4NGG or 7NGG, and their adhesion onto gelatin/vitronectin was measured after 30 min. As shown in FIG. 26, both peptides (4N1-1 and 7N3), corresponding to the two CD47-activating sites in the carboxyterminus of thrombospondin-1, stimulated BM-MNC adhesion significantly compared with BSA ($p<0.05$). There was no significant modulation of BM-MNC adhesion with the mutated peptides.

Figure 27:
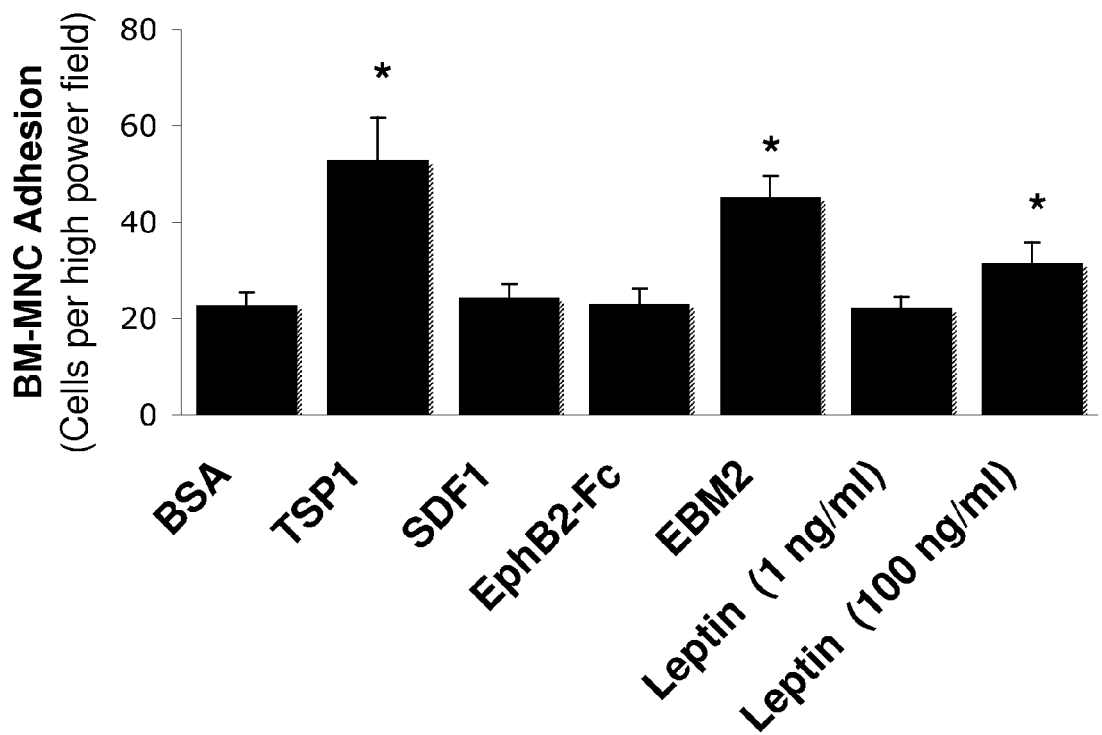
FIG. 27 represents BM-MNC adhesion onto gelatin-vitronectin for 30 min after pre-treatment for 2 hours with recombinant TSP1, SDF1, EphB2-Fc, VEGF-rich medium EBM2, or recombinant mouse leptin BSA as control (* p<0.05 vs BSA).

For comparison purposes, BM-MNC were pre-treated for 2 h with BSA (control), human recombinant TSP1, or other factors known to modulate progenitor cell adhesion or differentiation such as recombinant human stroma-derived factor 1α (SDF1; 100 ng/ml), recombinant chimeric ephrin-B2-Fc (EphB2-Fc; 3 µg/ml), VEGF-rich culture medium EBM2 (50%), or recombinant human leptin (1 and 100 ng/ml). BM-MNC adhesion onto gelatin/vitronectin was measured after 30 min. As shown in FIG. 27, EBM2 medium and leptin (100 ng/ml) stimulated a moderate increase in BM-MNC adhesion (less than a doubling), compared with BSA ($p<0.05$) or with the stimulations obtained with peptide 4N1-1 (FIG. 7). There was no significant modulation of BM-MNC adhesion with SDF1 or EphB2-Fc.

Figure 8:
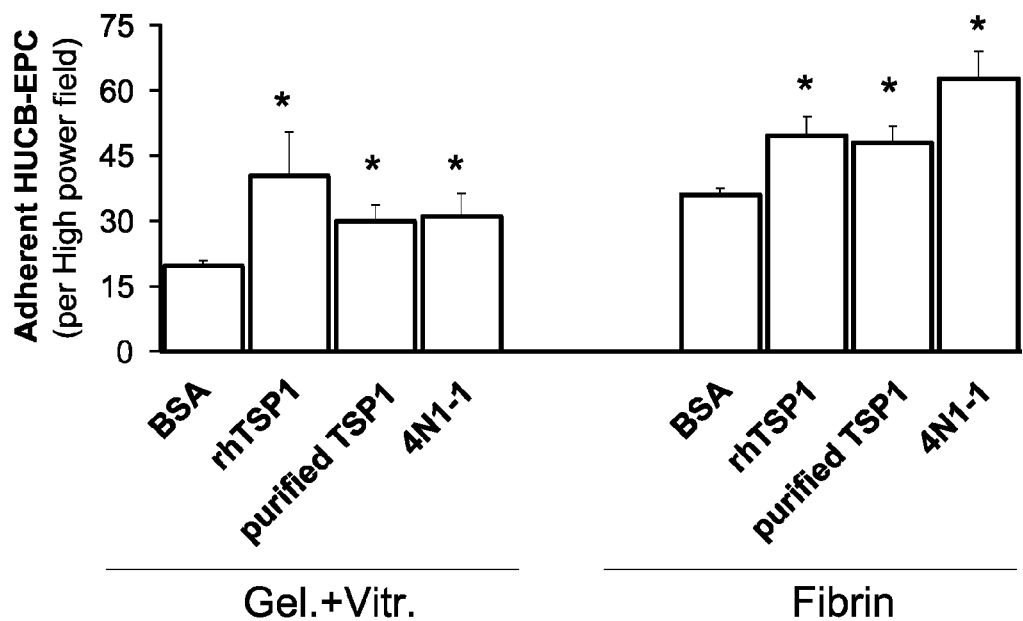
FIG. 8 represents HUCB-EPC adhesion onto gelatin-vitronectin or fibrin gels for 15 min after pre-treatment for 2 hours with BSA, human recombinant or purified TSP1, or peptide 4N1-1. (* p<0.05 vs BSA).

Effects of Pre-Incubating HUCB-EPC with Human Recombinant or Purified TSP1, or Peptide 4N1-1 on their Adhesion onto Gelatin/Vitronectin and Fibrin Gels:

HUCB-EPC were pre-treated for 2 h with human recombinant or purified TSP1 or with peptides 4N1-1, and their adhesion onto gelatin/vitronectin or fibrin gels was measured after 15 min. As shown on FIG. 8, pre-treatments with recombinant or purified TSP1, as well as with peptide 4N1-1 significantly stimulated adhesion compared with BSA, both onto gelatin-vitronectin (+106.3%; +52.5%; and +58.5%, $p<0.05$, respectively), and onto fibrin (+37.6%; +33.3%; and +73.8%, $p<0.05$, respectively). The range of stimulations obtained with either type of TSP1 or peptide 4N1-1 were comparable on both types of matrix.

Figure 28:
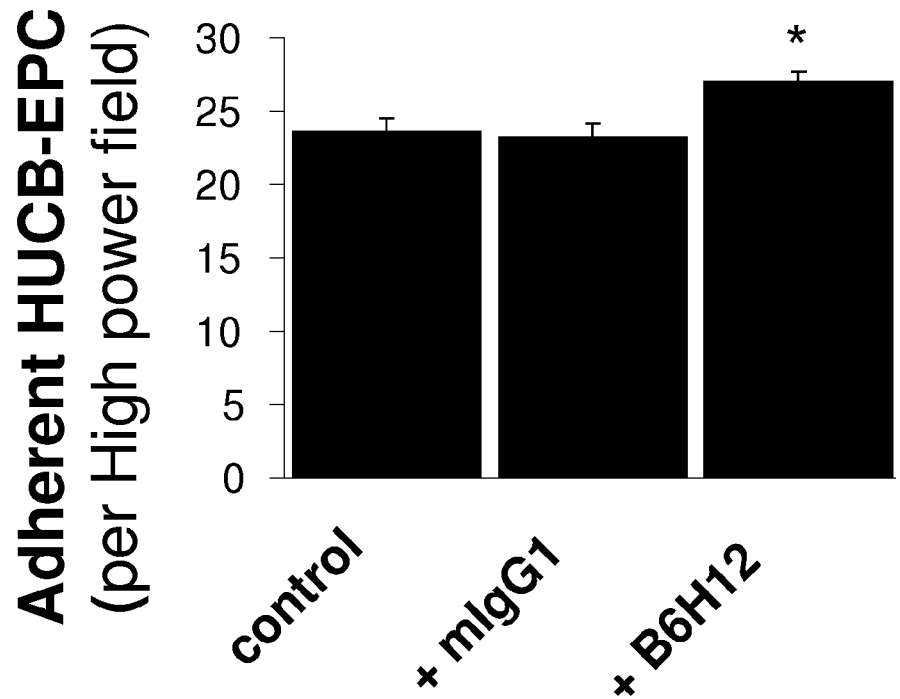
FIG. 28 represents HUCB-EPC adhesion onto gelatine-vitronectin for 15 min after pre-treatment for 30 min with control BSA, mouse mononclonal anti-human CD47 IgG1 clone B6H12, or matched control isotype mouse IgG1 (* p<0.05 vs BSA)

HUCB-EPC were pre-treated for 2 h at 37° C. in an incubator with 5% $CO_2$, in the presence of control BSA (1%), or with mouse monoclonal anti-human CD47 IgG1 B6H12 (40

μg/ml), or matched control isotype mouse IgG1 (40 μg/ml), before PBS washes and culture. As shown on FIG. 28, pre-treatments with B6H12 stimulated adhesion onto gelatin-vitronectin significantly compared with BSA or control mouse IgG1 (+14.6% or +16.6%, $p<0.05$, respectively). This suggested that anti-CD47 antibodies can function as agonists and display pro-adhesive effects similar to agonist peptides.

Figure 9:
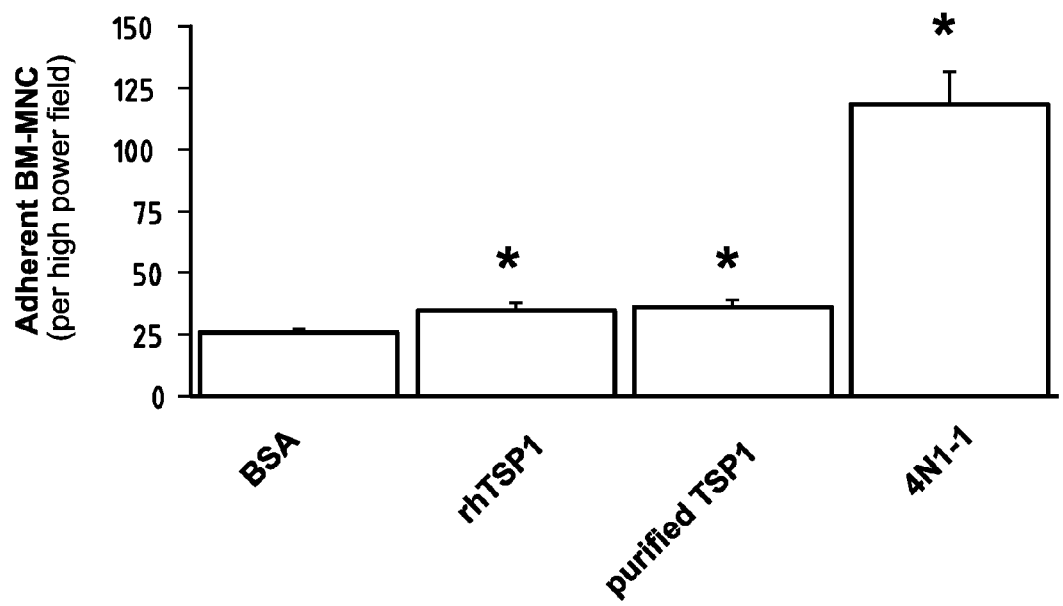
FIG. 9 represents BM-MNC adhesion onto IL1β-activated murine endothelial monolayers for 30 min after pre-treatment for 2 hours with human recombinant or purified TSP1, or peptide 4N1-1, or BSA; (*p<0.05 vs BSA).
Figure 10:
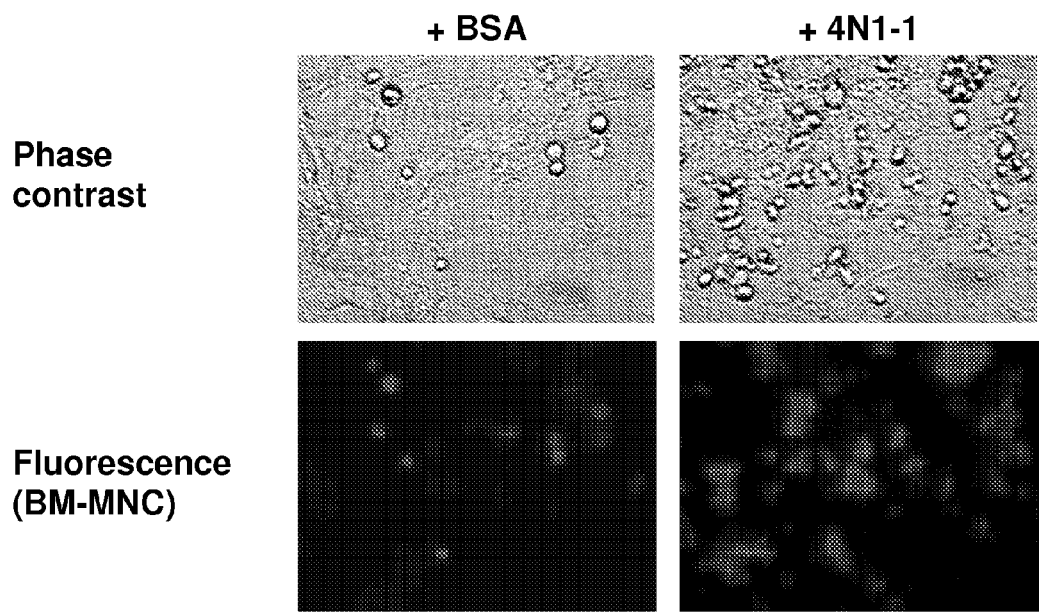
FIG. 10 represents photomicrographs of fluorescent-labelled BM-MNC adhesion onto IL1β-activated murine endothelial monolayers for 30 min after pre-treatment for 2 hours with peptide 4N1-1 or BSA (×400 magnification).

Effects of Pre-Incubation of BM-MNC with Human Recombinant or Purified TSP1, or with the Peptide 4N1-1 on their Adhesion onto Endothelial Monolayers:

BM-MNC were pre-treated for 2 h with recombinant or purified human TSP1 (10 μg/ml), or with peptide 4N1-1 (100 μM), and measured their adhesion after 30 min onto interleukin-1β-pre-activated murine endothelial monolayers. As shown in FIG. 9, pre-treatment with peptide 4N1-1 strongly stimulated adhesion (+359.5%, $p<0.05$) compared with BSA. Recombinant and purified TSP also induced significant stimulations (+34.2% and +40.5%, $p<0.05$, respectively). The effect of 4N1-1 on BM-MNC adhesion onto murine endothelial monolayers could be evidenced by fluorescence microscopy (FIG. 10).

Figure 22:
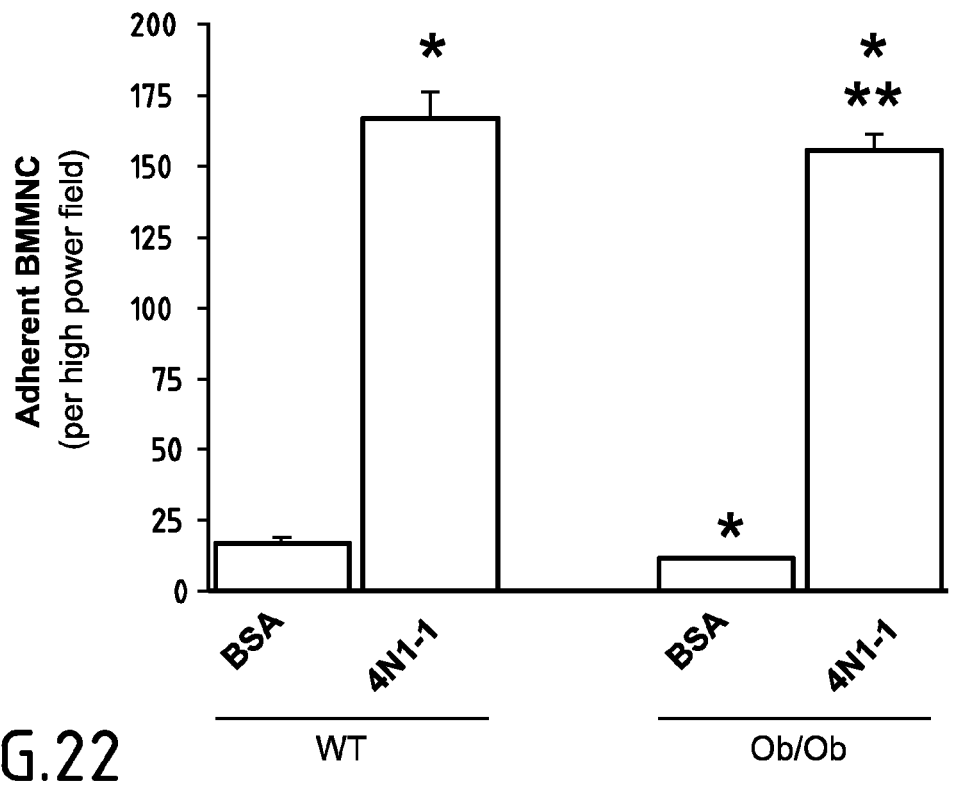
FIG. 22 represents the adhesion of BM-MNC derived from wild type or Ob/Ob leptin-deficient obese mice onto gelatin-vitronectin for 30 min after pre-treatment for 2 hours with peptide 4N1-1 or BSA as control (* p<0.05 vs BSA control; ** p<0.05 wild type vs Ob/Ob).
Figure 23:
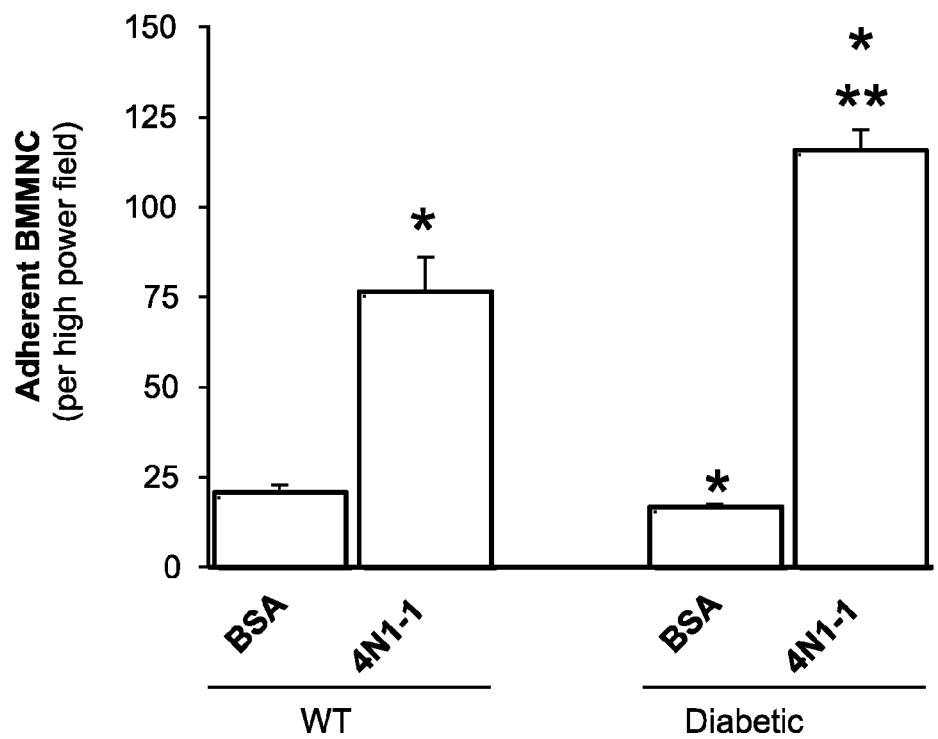
FIG. 23 represents the adhesion of BM-MNC derived from non diabetic, or diabetic streptozotocine-treated wild type mice onto gelatin-vitronectin for 30 min after pre-treatment for 2 hours with peptide 4N1-1 or BSA as control (* p<0.05 vs BSA control; ** p<0.05 non-diabetic vs diabetic).

Effects of Pre-Incubatinq BM-MNC Derived from Diabetic or Obese Mice with TSP1, or Peptide 4N1-1 on their Adhesion onto Gelatin/Vitronectin:

The adhesion of mouse BM-MNC derived from transgenic obese mice (Ob/Ob genotype, leptin-deficient) and diabetic mice (streptozotocine-induced type 1 diabetes) was evaluated in vitro. BM-MNC were pre-incubated with control BSA or 4N1-1 for 2 h before measuring their adhesion on gelatin/vitronectin matrix for 30 min. Obese Ob/Ob BM-MNC showed reduced adhesion (−31%; $p<0.05$) compared to wild type controls in vitro (FIG. 22), consistent with impairment of EPC function. However, adhesion was dramatically enhanced by pre-treatment with 4N1-1 at least as strongly as wild type BM-MNC (894.7% and 1,245.0% respectively compared to relevant BSA controls, $p<0.05$ versus control). Diabetic BM-MNC derived from streptozotocine-treated mice (FIG. 23) showed only a non-significant trend for reduced basal adhesion levels compared with non diabetic cells (−19%; $p>0.05$). However, adhesion of diabetic BM-MNC was dramatically enhanced by pre-treatment with 4N1-1, and diabetic cells responded significantly more to 4N1-1 than non-diabetic cells (270.3% versus 587.8%, respectively, compared to their relevant BSA controls; $p<0.05$ versus control, and $p<0.05$ between cells types).

Example 2

Expression of Cell Surface Adhesion Proteins in BM-MNC after Stimulation with TSP1 or Peptides 4N1-1 and 4N1-2

Figure 11:
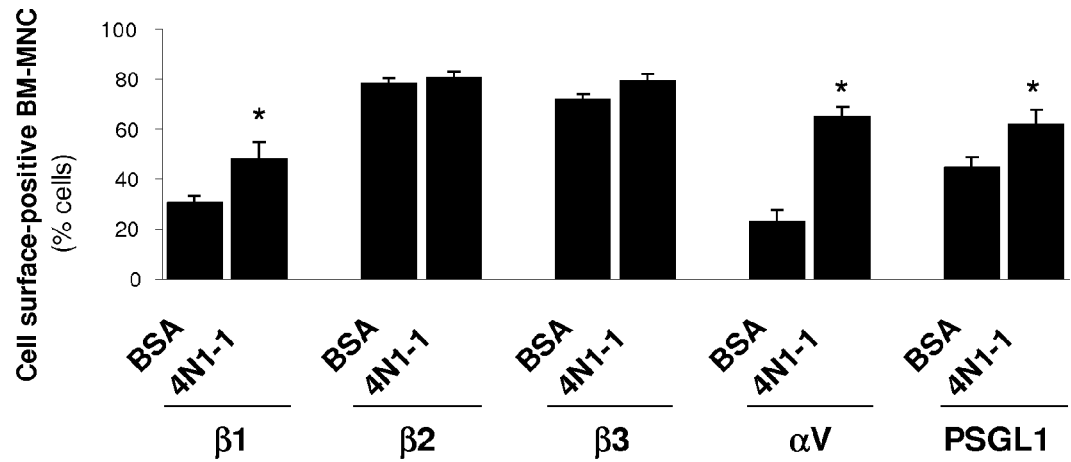
FIG. 11 represents the expression of integrins $\beta_1$, $\beta_2$, $\beta_3$ and $\alpha_v$, as well as PSGL1 at the surface of BM-MNC prior and after stimulation with peptide 4N1-1 or BSA for 30 min, (* p<0.05 vs BSA).

After the inventors observed increased BM-MNC adhesion following pre-treatment with peptide 4N1-1, they decided to determine whether the peptide modulates adhesion protein expression at their surface. Thus, BM-MNC were pre-treated for 30 min with control BSA or peptide 4N1-1 (50 μM), and integrin and PSGL1 expression was analyzed by immunolabelling and FACS. As shown in FIG. 11, pre-treatment with peptide 4N1-1 stimulated integrin $\beta_1$-expression (from 30.7% to 48.1%, $p<0.05$), integrin $\alpha_v$-expression (from 22.8% to 64.8%, $p<0.05$), and PSGL1 (from 44.4% to 61.8%, $p<0.05$), compared with BSA. In addition, 4N1-1 showed a trend in stimulating integrin $\beta_3$-expression (from 72.0% to 79.4%), although not significant ($p=0.07$), whereas 4N1-1 failed to modulate integrin $\beta_2$-expression in these experiments ($p>0.5$).

Figure 30:
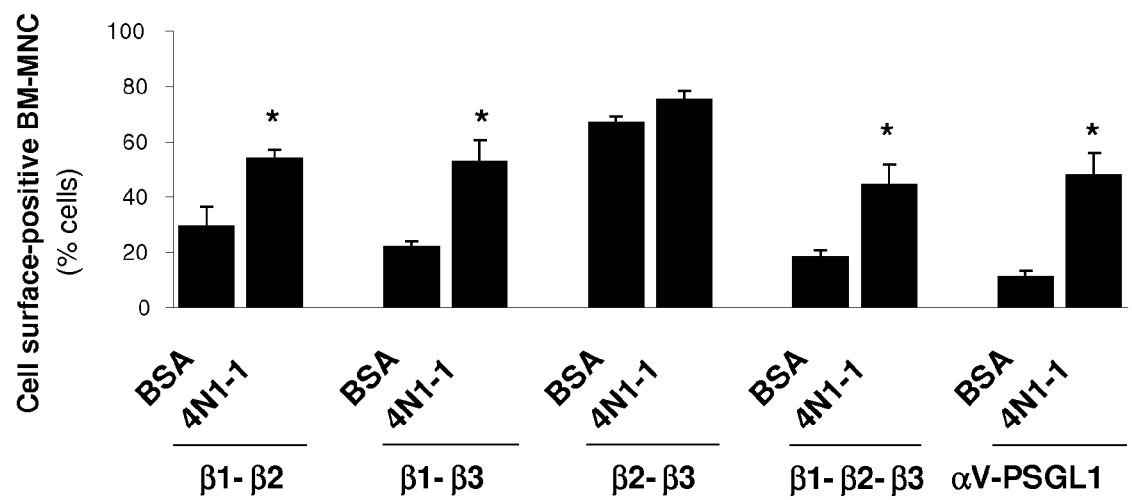
FIG. 30 represents the co-expression of integrins $\beta_1$, $\beta_2$ and $\beta_3$, as well as $\alpha_v$ and PSGL1 at the surface of BM-MNC prior and after stimulation with peptide 4N1-1 or BSA for 30 min, (* p<0.05 vs BSA).

As shown in FIG. 30, pre-treatment with peptide 4N1-1 stimulated the simultaneous co-expression of integrin $\beta_1$ and $\beta_2$ (from 29.8% to 54.4%, $p<0.05$), of integrin $\beta_1$ and $\beta_3$ (from 22.4% to 53.1%, $p<0.05$), of integrin $\beta_2$ and $\beta_3$ (from 67.4% to 75.6%, $p<0.05$), or of integrin $\beta_1$ and $\beta_2$ and $\beta_3$ (from 18.8% to 44.8%, $p<0.05$), integrin $\alpha_v$ and PSGL1 (from 11.5% to 48.4%, $p<0.05$), compared with BSA. Thus, 4N1-1 strongly stimulated the simultaneous expression of multiple adhesion receptors at the BM-MNC surface.

Example 3

Modulation of BM-MNC Spreading after Stimulation with Peptide 4N1-1

Figure 14:
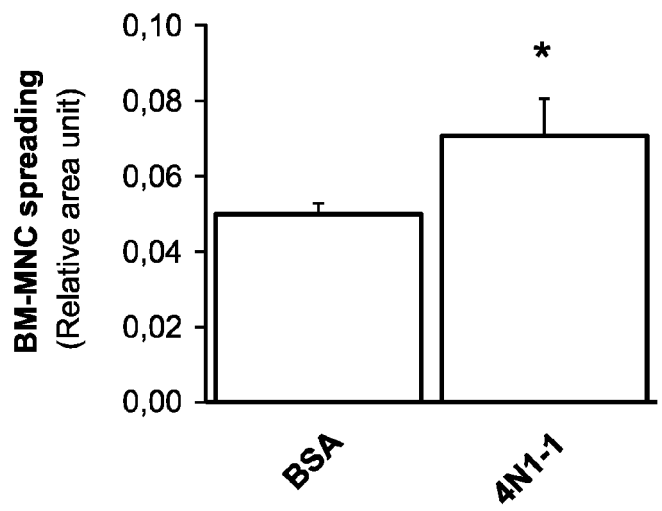
FIG. 14 represents BM-MNC spreading onto gelatin-vitronectin matrix, after pre-treatment for 2 hours with BSA or peptide 4N1-1 (50 μM) and 30 min of adhesion, by measure of cell area by image analysis, (* p<0.05 vs BSA).

After observing increased BM-MNC adhesion following treatment with peptide 4N1-1, the inventors examined the extent of cell spreading onto gelatin/vitronectin matrix in vitro, as triggered by peptide 4N1-1. BM-MNC were pre-treated with 4N1-1 (100 μM), or control BSA and left to adhere for 30 min (FIG. 14). 4N1-1 stimulated an increase in cell spreading of 41% versus BSA ($p<0.05$), in area occupied by individual cells.

Example 4

Modulation of BM-MNC Shape after Stimulation with Peptide 4N1-1

Figure 15:
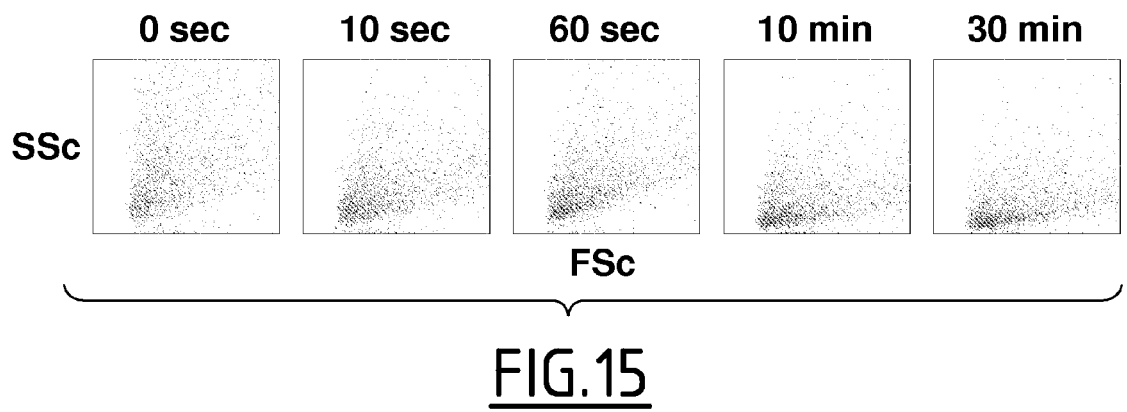
FIG. 15 represents rapid changes in BM-MNC shape, as measured by FACS Foward Scatter (FSc) and Side Scatter (SSc) after pre-treatment for 0, 10, or 60 sec, or 10 or 30 min with peptide 4N1-1 (50 μM). Data shown as FSc and SSc dot distribution.
Figure 16:
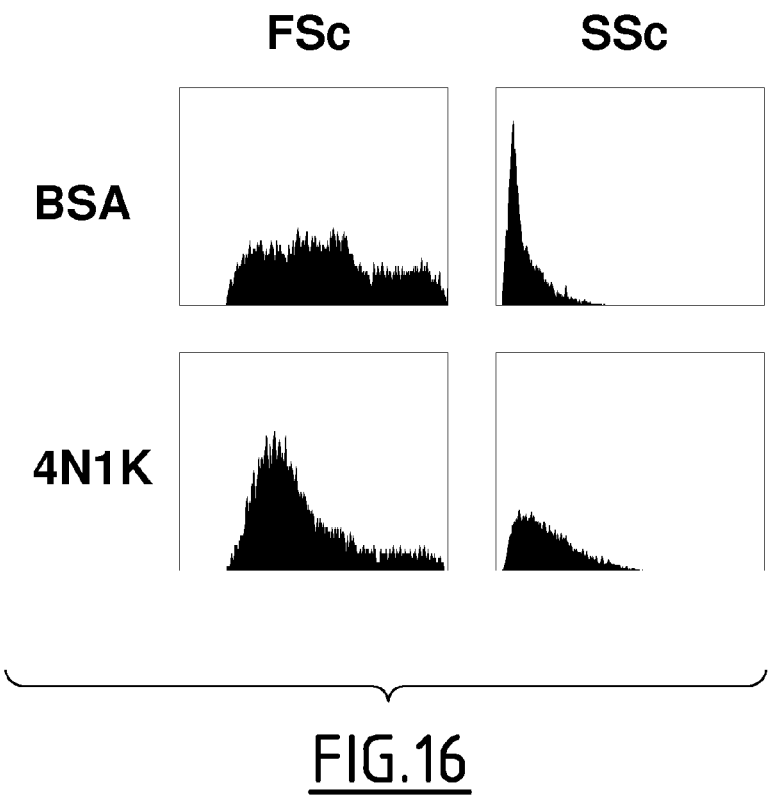
FIG. 16 represents rapid changes in BM-MNC shape, as measured by FACS Foward Scatter (FSc) and Side Scatter (SSc) after pre-treatment for 60 sec with or without peptide 4N1-1 (50 μM). Data shown as individual profiles of FSc and SSc distribution.

After observing increased BM-MNC adhesion following treatment with peptide 4N1-1, the inventors examined cell shape changes triggered by peptide 4N1-1. BM-MNC were pre-treated with 4N1-1 (50 μM) for increasing times and immediately analyzed by FACS to determine their shape distribution in the Forward and Side Scatter channels (FSc and SSc) of a cell sorter (FIG. 15). As short as 60 seconds of treatment was sufficient to trigger significant changes in cell shape, suggesting rapid and active remodelling of the cytoskeleton. FIG. 16 shows the shape distribution of BM-MNC in individual FSc and SSc after incubation with BSA or 4N1-1 for 10 min, revealing an overall homogenization of BM-MNC shape and structure across the population.

Example 5

Modulation of BM-MNC Apoptosis after Stimulation with Peptide 4N1-1

Figure 13:
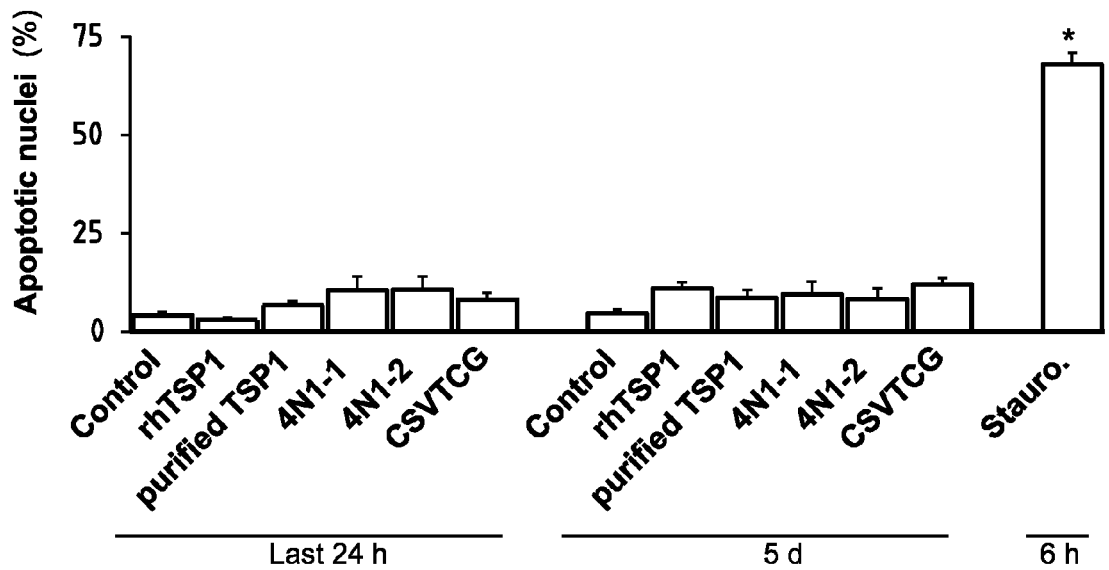
FIG. 13 represents apoptosis of BM-MNC after 5 days in culture, following treatment with control BSA, recombinant or purified human TSP1, or peptides 4N1-1, 4N1-2 or CSVTCG for 2 h prior culture (left panel), or continuously for 5 days (middle panel), or with staurosporine for the final 6 h (right bar), (* p<0.05 vs BSA).

After observing increased BM-MNC adhesion following treatment with peptide 4N1-1, the inventors examined the extent of apoptosis triggered by peptide 4N1-1. BM-MNC were pre-treated with 4N1-1 (100 μM), or control BSA and cultured for 5 days, or cultured for 5 days in the continued presence of 4N1-1, or for 6 h with staurosporine (FIG. 13). 4N1-1 and 4N1-2 peptides did not stimulate apoptosis significantly compared to BSA, even after 5 days of culture.

Figure 29:
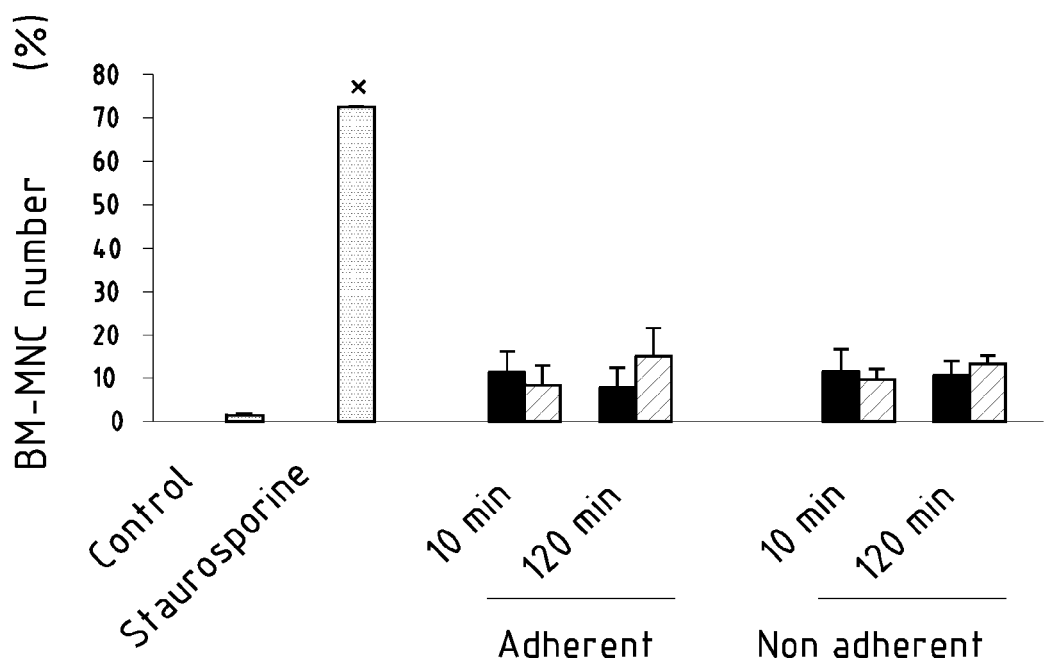
FIG. 29 represents apoptosis of BM-MNC in suspension after 0 hour (control) or 6 hours in the presence of staurosporine, or after 24 hours in culture following prior treatment with peptides 4N1-1 (hatched bars) or 4N1-2 (black bars) for 10 and 120 min. After culture, adherent and non-adherent cells were analyzed separately (×p<0.05 vs control).

The inventors examined the extent of apoptosis in BM-MNC treated with peptide 4N1-1 and 4N1-2, using a second method. BM-MNC were pre-treated with 4N1-1 or 4N1-2 (50 μM) for 10 or 120 min, and cultured in full EBM2 medium, with serum and growth factors for up to 24 hours, to allow potential apoptotic reactions to proceed (FIG. 29). Untreated fresh cells served as control and the induction of apoptosis by staurosporine for 6 hours in suspended was also monitored. After culture, adherent and non-adherent cells were harvested and analyzed separately. Peptides 4N1-1 and 4N1-2 did not stimulate apoptosis significantly compared to staurosporine or control, neither in adherent nor non-adherent cells, even after 120 min of incubation. No induction of apoptosis was found for treatments with CD47 agonists that induce optimal stimulation of BMC adhesion. In contrast, only 6 hours of treatment with pro-apoptotic staurosporine induced a 72.5% increase in cell death (* $p<0.05$).

Example 6

Effects of TSP1 and Peptides 4N1-1, 4N1-2 and CSVTCG on the Endothelial Differentiation of BM-MNC Following the previous observation that TSP1 and peptide 4N1-1 stimulate BM-MNC adhesion in vitro, the inventors measured the endothelial differentiation of treated BM-MNC. BM-MNC were cultured for 5 days, following a 2 h pre-treatment with recombinant or purified TSP1, or with peptides 4N1-1, 4N1-2, or CSVTCG (a peptide derived from the TSP1 sequence). EPC-differentiated BM-MNC were identified by fluorescence microscopy after double-labelling for DiI-Ac-LDL incorporation and BS1 lectin binding.

Figure 12:
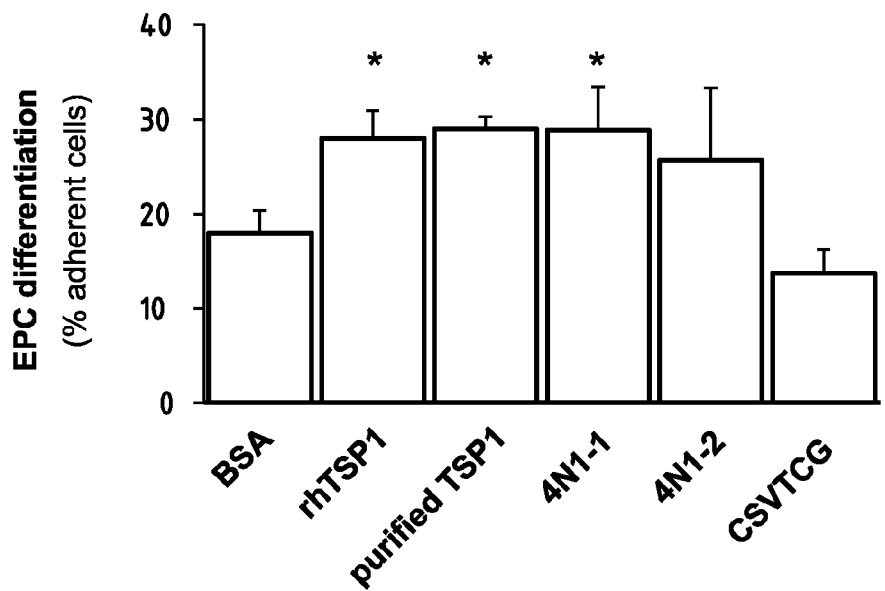
FIG. 12 represents endothelial differentiation of BM-MNC cultured for 5 days, after pre-treatment for 2 h with control BSA, recombinant or purified human TSP1, or peptides 4N1-1, 4N1-2 or CSVTCG. (* p<0.05 vs BSA, or Controls).

A trend of recombinant and purified TSP1 as well as 4N1-1 to stimulate endothelial differentiation after 2 h pre-treatment was observed (+28.0%; +28.9%; and 28.9% vs BSA, respectively; $p<0.05$) (FIG. 12).

Example 7

Modulation of BM-MNC Recruitment by TSP1 During Experimental Thrombosis

The inventors aimed to evidence the recruitment of BM-MNC at sites of thrombosis on the vascular wall, and the contribution of TSP1 to this process. To this end, fluorescence-labelled BM-MNC were injected to wild type or TSP1-deficient mice via the retro-orbital sinus. Lesions were then induced with $FeCl_3$ in mesenteric veins in wild type C57BL/6 mice, and BM-MNC recruitment was monitored locally as blood coagulation progressed. Anaesthetized mice with exposed mesenteric vessels were placed under the lense of an inverted fluorescence microscope to locate the borders of the lesion site and record BM-MNC interactions with the vascular wall in real time.

Figure 17:
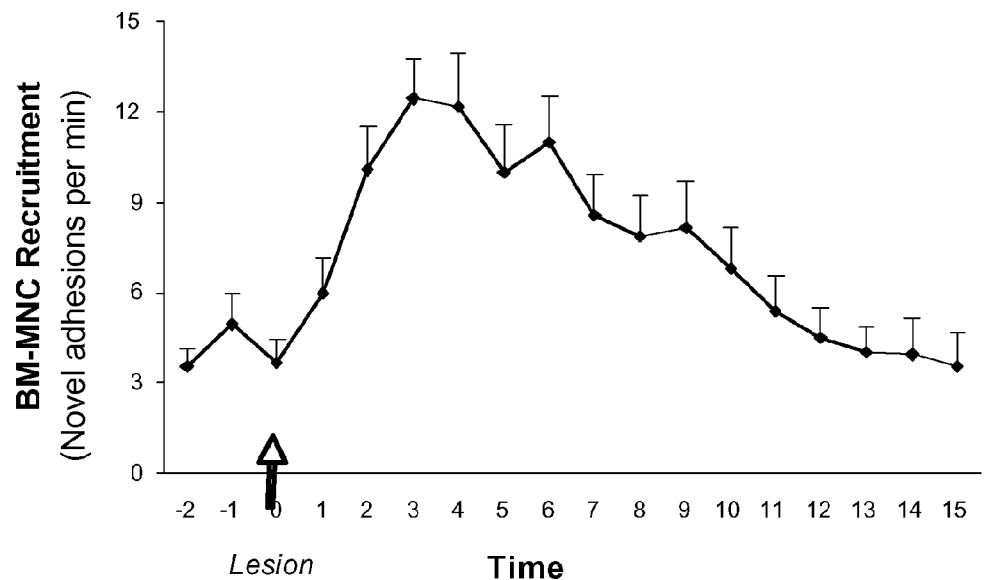
FIG. 17 represents the time-dependent recruitment of BM-MNC in mesenteric veins of C57BL/6 wild type mice before (−2 to 0 min) and after FeCl$_3$-induced thrombosis, observed by intra-vital microscopy (new cell interactions per minute, every minute) (* p<0.05 vs t=0 min).

Pre-Treatment with Peptide 4N1-1 Stimulates BM-MNC Recruitment to Thrombosed Vascular Walls As shown in FIG. 17, the specific recruitment of BM-MNC onto thrombosed vascular surfaces was evaluated in $FeCl_3$-challenged C57BL/6 wild type mouse mesenteric veins. Experimental thrombosis translated into increased rates of BM-MNC interacting with and rolling along thrombosed vascular surfaces (number of new interactions per minute, every minute), compared to either the same vascular segment before thrombosis, or with uninjured adjacent segments. BM-MNC recruitment to thrombosed surfaces reached a peak between 2 and 6 min post-thrombosis induction (+241.8%; vs uninjured; $p<0.05$), followed by a decrease back to basal levels after 12 min.

Figure 18:
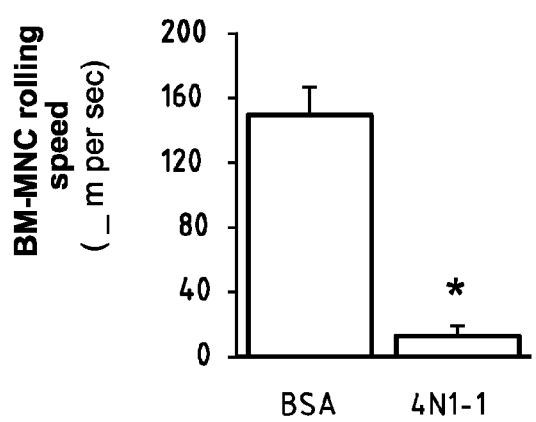
FIG. 18 represents BM-MNC rolling speeds on thrombosed surfaces in C57BL/6 mouse mesenteric veins, after pre-treatment for 2 hours with peptide 4N1-1 or BSA, (average rolling speed during the initial 10 min post-injury). (* p<0.05, vs BSA).
Figure 19:
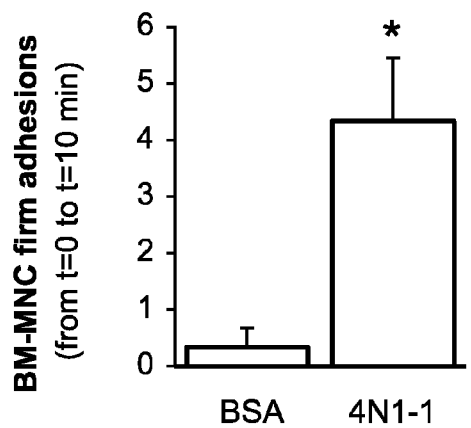
FIG. 19 represents BM-MNC numbers of firm adhesions onto thrombosed surfaces in C57BL/6 mouse mesenteric veins, after pre-treatment for 2 hours with peptide 4N1-1 or BSA, (cumulated firm adhesions during the initial 10 min post-injury). (*p<0.05, vs BSA).

The effects of peptide 4N1-1 pre-treatment on the type of interaction of BM-MNC with thrombosed vascular surfaces during the initial 10 min post-injury, compared with control BSA was further characterized. Thus, peptide 4N1-1 strongly decreased the average BM-MNC rolling speed by over 12 fold at sites of vascular thrombosis (from 149.8 to 12.8 μm/sec; $p<0.05$) (FIG. 18) and sharply increased by over 14 fold the number of firm adhesions (from 0.3 to 4.3 firm adhesions; $p<0.05$) (FIG. 19). This illustrated the increased capacity of 4N1-1-treated BM-MNC to interact with and bind firmly to thrombosed vascular surfaces.

Example 8

Stimulation of the Pro-Angiogenic Function of BM-MNC in Cell Therapy with Peptide 4N1-1

Figure 20:
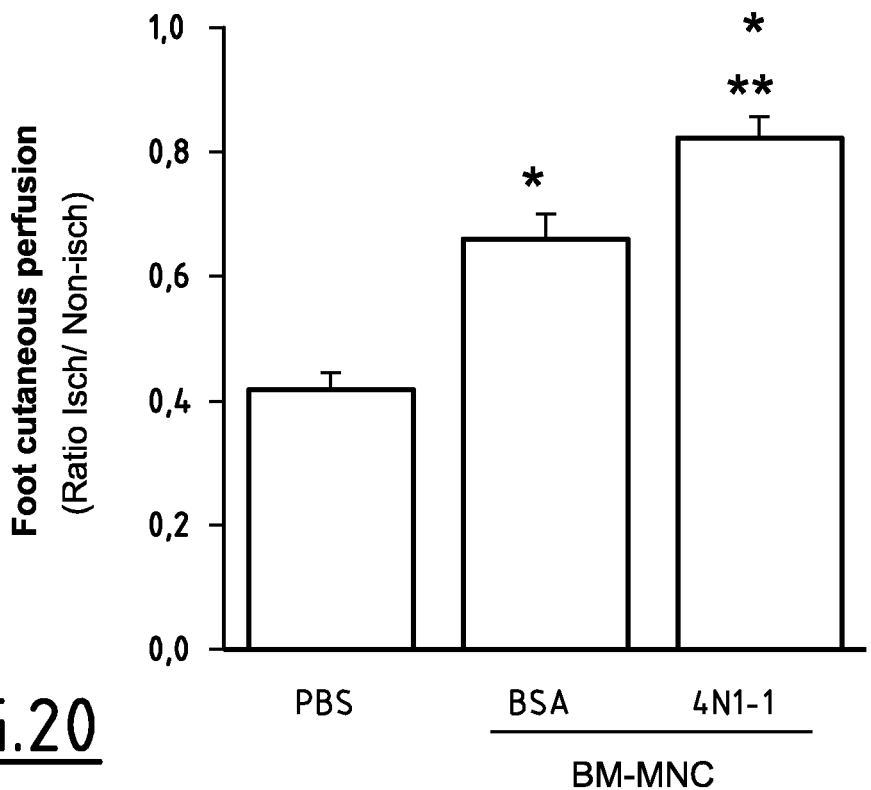
FIG. 20 represents ischemic hindlimb cutaneous blood flow, 14 days after ligation and injection of BM-MNC pre-treated for 2 hours with BSA or peptide 4N1-1. (* p<0.05, vs BSA).
Figure 21:
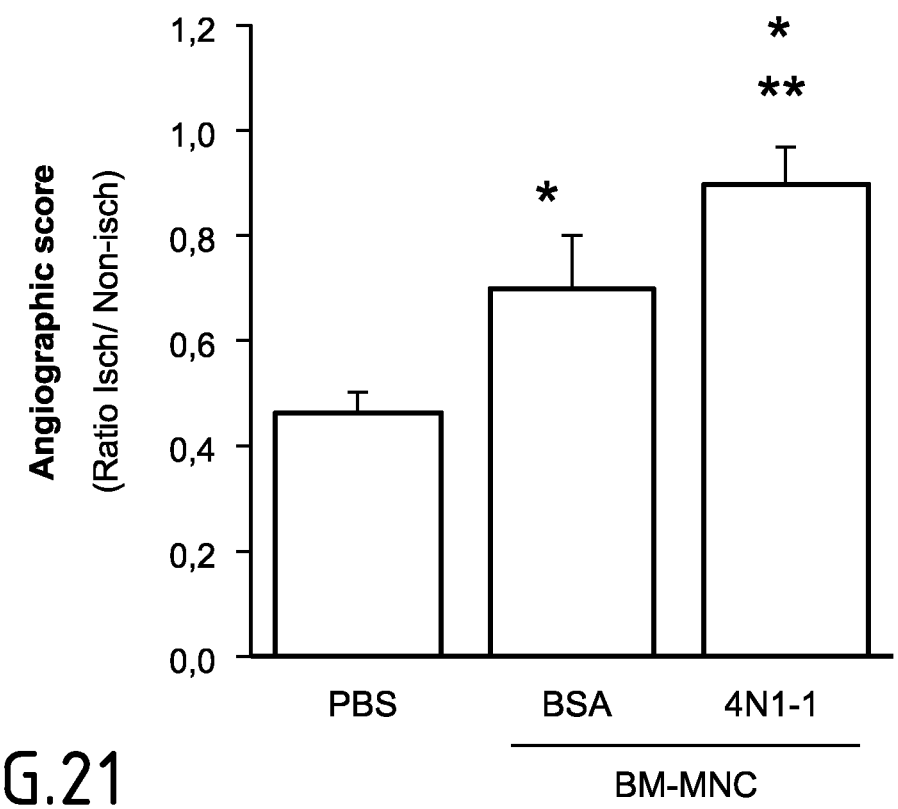
FIG. 21 represents micro-angiographic scores, 14 days after ligation and injection of BM-MNC pre-treated for 2 hours with BSA or 4N1-1, (* p<0.05, vs BSA). The extent of the perfused vascular network is quantified via X-ray image analysis.

The effects of peptide 4N1-1 on the pro-angiogenic function of BM-MNC and their efficacy in cell therapy were then studied. A murine model of hindlimb ischemia was used. The right femoral arteries of C57BL/6 mice were ligated and neo-angiogenesis was stimulated with the intra-vascular administration of BM-MNC pre-treated with peptides 4N1-1, or control BSA through the retro-orbital sinus. Intact left femoral arteries were used as controls. Post-ischemic neovascularization was evaluated after 14 days, with two protocols: (i) laser-doppler imaging of foot cutaneous flow for the evaluation of hindlimb reperfusion (FIG. 20), and (ii) X-ray microangiography of the functional vascular network for the determination of a neo-vascularization score (FIG. 21). Pre-treating BM-MNC with peptide 4N1-1 stimulated their effect on cutaneous reperfusion significantly compared with BSA (+30.20%, $p<0.05$) and resulted in a more extended perfused vascular network (+41.45%, $p<0.05$).

Example 9

Modulation of BM-MNC Adhesion and Recruitment During Inhibition of TSP1

Figure 24:
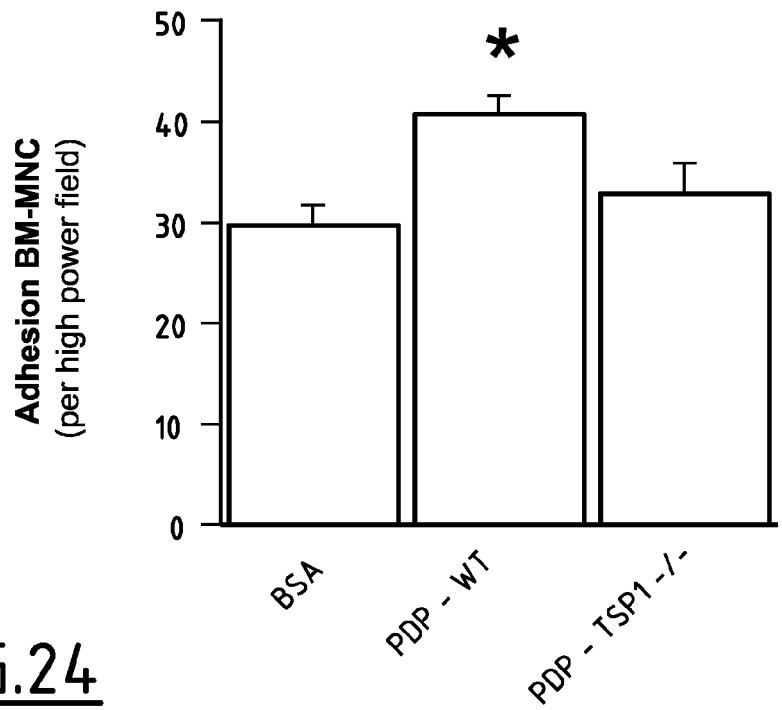
FIG. 24 represents BM-MNC adhesion onto fibrin gels for 30 min after pre-treatment for 2 hours with BSA or platelet degranulation products (PDP) derived from wild type or TSP1−/− SWISS mice. (* p<0.05 vs BSA).

Effects of TSP1 Genetic Deletion on the Adhesion of BM-MNC onto Fibrin Gels after Pre-Incubation with Platelet Degranulation Products:

BM-MNC were pre-treated for 2 h with platelet degranulation products (PDP) obtained from either wild type or TSP1-deficient platelets (dilution factor 1:10 in EBM), and their adhesion onto fibrin gels was measured after 30 min. Pre-treatment with platelet degranulation products obtained from wild type platelets (PDP-WT) significantly stimulated BM-MNC adhesion (+36.9%, $p<0.05$), but not those derived from TSP1−/− platelets (PDP-TSP1−/−), compared with BSA (+10.4%, $p=0.21$ vs BSA; and $p<0.05$ vs PDP-WT) (FIG. 24).

Effects of TSP1 Genetic Deletion on BM-MNC Recruitment to the Thrombosed Vascular Wall To determine the contribution of endogenous TSP1 in the recruitment of BM-MNC to thrombosed vascular walls, mesenteric veins of wild type and TSP1-deficient SWISS mice were used, after wild type BM-MNC administration.

Figure 25:
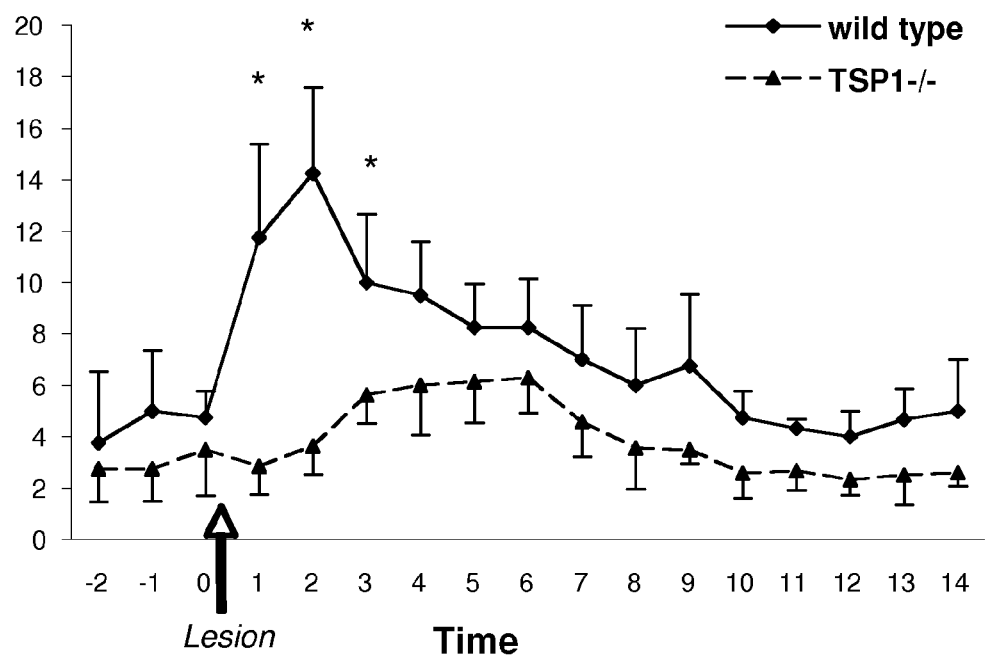
FIG. 25 represents the time-dependent recruitment of wild type BM-MNC in mesenteric veins of wild type or TSP1−/− SWISS mice before (−2 to 0 min) and after FeCl$_3$-induced thrombosis, observed by intra-vital microscopy (new cell interactions per minute, every minute). (*p<0.05 vs wild type).

As shown in FIG. 25, in wild type mice, the inventors observed a specific recruitment of circulating BM-MNC at lesion sites with a maximal rate of recruitment between 1 and 3 min after thrombosis induction (+250.0% maximum; $p<0.05$), followed by a reduction back to basal levels after 8 min. A near total abrogation of this phenomenon in TSP1-deficient mice compared to wild type mice was measured. This downregulation of BM-MNC recruitment in the absence of TSP1 translated into a decrease in the maximal rate of cell recruitment at the lesion site per minute, (−71.0% vs wild type mice, $p<0.05$), and in a delay of at least 3 min in the onset and end of the recruitment period compared to wild type mice. This suggests that removing or otherwise ablating TSP1-CD47 signals, e.g. through genetic deletion, may block local progenitor cell adhesion and engraftment.

The invention claimed is:

1. An in vitro method for preparing progenitor cells having an increased adhesivity, comprising a step of contacting progenitor cells with an agonist of the CD47/IAP receptor for from 10 seconds to 2 hours, followed by a step of selecting adherent cells among prepared cells, thereby yielding progenitor cells presenting an increased adhesivity, wherein the agonist of the CD47/IAP receptor is selected from the group consisting of a polypeptide consisting of the sequence RFYVVMWK (SEQ ID NO: 3); the Thrombospondin-1 protein, and a Thrombospondin-1 protein derivative comprising RFYVVMWK (SEQ ID NO: 3).

2. The method of claim 1, wherein the prepared progenitor cells are intended for engraftment in a target tissue of an individual.

3. The method of claim 2, wherein the prepared progenitor cells are liable to differentiate into mature cells in the target tissue and differentiation of the prepared cells is accelerated with respect to similar cells which have not been prepared according to said method.

4. The method of claim 2, wherein the progenitor cells originate from the individual.

5. The method according to claim 1, wherein the progenitor cells originate from tissues selected from the group constituted of adipose tissue, bone marrow, liver, and blood.

6. The method of claim 1, wherein the progenitor cells are liable to differentiate into endothelial cells.

7. The method claim 1, wherein the progenitor cells are bone marrow mononuclear cells.

8. An in vitro method for preparing progenitor cells having an increased adhesivity comprising a step of contacting progenitor cells with an agonist of the CD47/IAP receptor for from 10 seconds to 2 hours, followed by a step of selecting adherent cells among prepared cells thereby yielding progenitor cells having an increased adhesivity, wherein the agonist of the CD47/IAP receptor is the TSP-1 protein; or a polypeptide consisting of the sequence RFYVVMWK (SEQ ID NO: 3).

* * * * *

SEQUENCE LISTING

<160> NUMBER OF SEQ ID NOS: 13

<210> SEQ ID NO 1
<211> LENGTH: 972
<212> TYPE: DNA
<213> ORGANISM: Homo sapiens

<400> SEQUENCE: 1

| | | | | | |
|---|---|---|---|---|---|
| atgtggcccc | tggtagcggc | gctgttgctg | ggctcggcgt | gctgcggatc | agctcagcta | 60 |
| ctatttaata | aaacaaaatc | tgtagaattc | acgttttgta | atgacactgt | cgtcattcca | 120 |
| tgctttgtta | ctaatatgga | ggcacaaaac | actactgaag | tatacgtaaa | gtggaaattt | 180 |
| aaaggaagag | atatttacac | ctttgatgga | gctctaaaca | agtccactgt | ccccactgac | 240 |
| tttagtagtg | caaaaattga | agtctcacaa | ttactaaaag | gagatgcctc | tttgaagatg | 300 |
| gataagagtg | atgctgtctc | acacacagga | aactacactt | gtgaagtaac | agaattaacc | 360 |
| agagaaggtg | aaacgatcat | cgagctaaaa | tatcgtgttg | tttcatggtt | ttctccaaat | 420 |
| gaaaatattc | ttattgttat | tttcccaatt | tttgctatac | tcctgttctg | gggacagttt | 480 |
| ggtattaaaa | cacttaaata | tagatccggt | ggtatggatg | agaaaacaat | tgctttactt | 540 |
| gttgctggac | tagtgatcac | tgtcattgtc | attgttggag | ccattctttt | cgtcccaggt | 600 |
| gaatattcat | aaagaatgc | tactggcctt | ggtttaattg | tgacttctac | agggatatta | 660 |
| atattacttc | actactatgt | gtttagtaca | gcgattggat | taacctcctt | cgtcattgcc | 720 |
| atattggtta | ttcaggtgat | agcctatatc | ctcgctgtgg | ttggactgag | tctctgtatt | 780 |
| gcggcgtgta | taccaatgca | tggccctctt | ctgatttcag | gtttgagtat | cttagctcta | 840 |
| gcacaattac | ttggactagt | ttatatgaaa | tttgtggctt | ccaatcagaa | gactatacaa | 900 |
| cctcctagga | aagctgtaga | ggaacccctt | aatgcattca | aagaatcaaa | aggaatgatg | 960 |
| aatgatgaat | aa | | | | | 972 |

<210> SEQ ID NO 2
<211> LENGTH: 323
<212> TYPE: PRT
<213> ORGANISM: Homo sapiens

<400> SEQUENCE: 2

Met Trp Pro Leu Val Ala Ala Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
                210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Gly Leu Val Tyr
                275                 280                 285

Met Lys Phe Val Ala Ser Asn Gln Lys Thr Ile Gln Pro Pro Arg Lys
290                 295                 300

Ala Val Glu Glu Pro Leu Asn Ala Phe Lys Glu Ser Lys Gly Met Met
305                 310                 315                 320

Asn Asp Glu

<210> SEQ ID NO 3
<211> LENGTH: 8
<212> TYPE: PRT
<213> ORGANISM: Artificial sequence
<220> FEATURE:
<223> OTHER INFORMATION: 4N1-1 peptide

<400> SEQUENCE: 3

Arg Phe Tyr Val Val Met Trp Lys
1               5

<210> SEQ ID NO 4
<211> LENGTH: 10
<212> TYPE: PRT
<213> ORGANISM: Artificial sequence
<220> FEATURE:
<223> OTHER INFORMATION: 4N1K peptide

<400> SEQUENCE: 4

Lys Arg Phe Tyr Val Val Met Trp Lys Lys
1               5                   10

<210> SEQ ID NO 5
<211> LENGTH: 1170
<212> TYPE: PRT
<213> ORGANISM: Homo sapiens

<400> SEQUENCE: 5

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
                20                  25                  30

Ile Phe Glu Leu Thr Gly Ala Ala Arg Lys Gly Ser Gly Arg Arg Leu
                35                  40                  45

Val Lys Gly Pro Asp Pro Ser Ser Pro Ala Phe Arg Ile Glu Asp Ala

-continued

```
                50                  55                  60
Asn Leu Ile Pro Pro Val Pro Asp Asp Lys Phe Gln Asp Leu Val Asp
 65                  70                  75                  80

Ala Val Arg Ala Glu Lys Gly Phe Leu Leu Leu Ala Ser Leu Arg Gln
                 85                  90                  95

Met Lys Lys Thr Arg Gly Thr Leu Leu Ala Leu Glu Arg Lys Asp His
                100                 105                 110

Ser Gly Gln Val Phe Ser Val Val Ser Asn Gly Lys Ala Gly Thr Leu
                115                 120                 125

Asp Leu Ser Leu Thr Val Gln Gly Lys Gln His Val Val Ser Val Glu
                130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
                180                 185                 190

Ser Ile Ala Arg Leu Arg Ile Ala Lys Gly Gly Val Asn Asp Asn Phe
                195                 200                 205

Gln Gly Val Leu Gln Asn Val Arg Phe Val Phe Gly Thr Thr Pro Glu
                210                 215                 220

Asp Ile Leu Arg Asn Lys Gly Cys Ser Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
                260                 265                 270

Ser Cys Asp Glu Leu Ser Ser Met Val Leu Glu Leu Arg Gly Leu Arg
                275                 280                 285

Thr Ile Val Thr Thr Leu Gln Asp Ser Ile Arg Lys Val Thr Glu Glu
                290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
                340                 345                 350

Cys Pro Ile Met Pro Cys Ser Asn Ala Thr Val Pro Asp Gly Glu Cys
                355                 360                 365

Cys Pro Arg Cys Trp Pro Ser Asp Ser Ala Asp Asp Gly Trp Ser Pro
                370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
                420                 425                 430

Lys Gln Asp Gly Gly Trp Ser His Trp Ser Pro Trp Ser Ser Cys Ser
                435                 440                 445

Val Thr Cys Gly Asp Gly Val Ile Thr Arg Ile Arg Leu Cys Asn Ser
                450                 455                 460

Pro Ser Pro Gln Met Asn Gly Lys Pro Cys Glu Gly Glu Ala Arg Glu
465                 470                 475                 480
```

```
Thr Lys Ala Cys Lys Lys Asp Ala Cys Pro Ile Asn Gly Gly Trp Gly
            485                 490                 495

Pro Trp Ser Pro Trp Asp Ile Cys Ser Val Thr Cys Gly Gly Gly Val
        500                 505                 510

Gln Lys Arg Ser Arg Leu Cys Asn Asn Pro Thr Pro Gln Phe Gly Gly
        515                 520                 525

Lys Asp Cys Val Gly Asp Val Thr Glu Asn Gln Ile Cys Asn Lys Gln
    530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
            565                 570                 575

Pro Gly Tyr Ser Gly Asn Gly Ile Gln Cys Thr Asp Val Asp Glu Cys
        580                 585                 590

Lys Glu Val Pro Asp Ala Cys Phe Asn His Asn Gly Glu His Arg Cys
        595                 600                 605

Glu Asn Thr Asp Pro Gly Tyr Asn Cys Leu Pro Cys Pro Pro Arg Phe
        610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
            645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
        675                 680                 685

Cys Gly Glu Asp Thr Asp Leu Asp Gly Trp Pro Asn Glu Asn Leu Val
        690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
            725                 730                 735

Ala Cys Asp Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
        755                 760                 765

Asp Val Gly Asp Arg Cys Asp Asn Cys Pro Tyr Asn His Asn Pro Asp
    770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
            805                 810                 815

Tyr Asn Val Asp Gln Arg Asp Thr Asp Met Asp Gly Val Gly Asp Gln
            820                 825                 830

Cys Asp Asn Cys Pro Leu Glu His Asn Pro Asp Gln Leu Asp Ser Asp
        835                 840                 845

Ser Asp Arg Ile Gly Asp Thr Cys Asp Asn Asn Gln Asp Ile Asp Glu
    850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
            885                 890                 895
```

-continued

```
Asp Asp Asp Asn Asp Gly Ile Pro Asp Lys Asp Asn Cys Arg Leu
            900             905             910

Val Pro Asn Pro Asp Gln Lys Asp Ser Asp Gly Asp Gly Arg Gly Asp
        915                 920                 925

Ala Cys Lys Asp Asp Phe Asp His Asp Ser Val Pro Asp Ile Asp Asp
    930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
                965                 970                 975

Trp Val Val Arg His Gln Gly Lys Glu Leu Val Gln Thr Val Asn Cys
            980                 985                 990

Asp Pro Gly Leu Ala Val Gly Tyr  Asp Glu Phe Asn Ala  Val Asp Phe
        995                 1000                1005

Ser Gly Thr Phe Phe Ile Asn  Thr Glu Arg Asp  Asp Asp Tyr Ala
        1010                1015                1020

Gly Phe Val Phe Gly Tyr Gln  Ser Ser Ser Arg Phe  Tyr Val Val
        1025                1030                1035

Met Trp Lys Gln Val Thr Gln  Ser Tyr Trp Asp Thr  Asn Pro Thr
        1040                1045                1050

Arg Ala  Gln Gly Tyr Ser Gly  Leu Ser Val Lys  Val Asn Ser
        1055                1060                1065

Thr Thr  Gly Pro Gly Glu His  Leu Arg Asn Ala Leu  Trp His Thr
        1070                1075                1080

Gly Asn  Thr Pro Gly Gln Val  Arg Thr Leu Trp His  Asp Pro Arg
        1085                1090                1095

His Ile  Gly Trp Lys Asp Phe  Thr Ala Tyr Arg Trp  Arg Leu Ser
        1100                1105                1110

His Arg  Pro Lys Thr Gly Phe  Ile Arg Val Val Met  Tyr Glu Gly
        1115                1120                1125

Lys Lys  Ile Met Ala Asp Ser  Gly Pro Ile Tyr Asp  Lys Thr Tyr
        1130                1135                1140

Ala Gly  Gly Arg Leu Gly Leu  Phe Val Phe Ser Gln  Glu Met Val
        1145                1150                1155

Phe Phe  Ser Asp Leu Lys Tyr  Glu Cys Arg Asp Pro
        1160                1165                1170

<210> SEQ ID NO 6
<211> LENGTH: 1170
<212> TYPE: PRT
<213> ORGANISM: Mus musculus

<400> SEQUENCE: 6

Met Glu Leu Leu Arg Gly Leu Gly Val Leu Phe Leu Leu His Met Cys
1               5                   10                  15

Gly Ser Asn Arg Ile Pro Glu Ser Gly Gly Asp Asn Gly Val Phe Asp
            20                  25                  30

Ile Phe Glu Leu Ile Gly Gly Ala Arg Arg Gly Pro Gly Arg Arg Leu
        35                  40                  45

Val Lys Gly Gln Asp Leu Ser Ser Pro Ala Phe Arg Ile Glu Asn Ala
    50                  55                  60

Asn Leu Ile Pro Ala Val Pro Asp Asp Lys Phe Gln Asp Leu Leu Asp
65                  70                  75                  80

Ala Val Trp Ala Asp Lys Gly Phe Ile Phe Leu Ala Ser Leu Arg Gln
                85                  90                  95
```

-continued

```
Met Lys Lys Thr Arg Gly Thr Leu Leu Ala Val Glu Arg Lys Asp Asn
            100                 105                 110

Thr Gly Gln Ile Phe Ser Val Ser Asn Gly Lys Ala Gly Thr Leu
            115                 120                 125

Asp Leu Ser Leu Ser Leu Pro Gly Lys Gln Gln Val Val Ser Val Glu
130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Lys Met Glu Ser
            165                 170                 175

Ala Glu Leu Asp Val Pro Ile Gln Ser Ile Phe Thr Arg Asp Leu Ala
            180                 185                 190

Ser Val Ala Arg Leu Arg Val Ala Lys Gly Asp Val Asn Asp Asn Phe
            195                 200                 205

Gln Gly Val Leu Gln Asn Val Arg Phe Val Phe Gly Thr Thr Pro Glu
            210                 215                 220

Asp Ile Leu Arg Asn Lys Gly Cys Ser Ser Ser Thr Asn Val Leu Leu
225                 230                 235                 240

Thr Leu Asp Asn Asn Val Val Asn Gly Ser Ser Pro Ala Ile Arg Thr
            245                 250                 255

Asn Tyr Ile Gly His Lys Thr Lys Asp Leu Gln Ala Ile Cys Gly Leu
            260                 265                 270

Ser Cys Asp Glu Leu Ser Ser Met Val Leu Glu Leu Lys Gly Leu Arg
            275                 280                 285

Thr Ile Val Thr Thr Leu Gln Asp Ser Ile Arg Lys Val Thr Glu Glu
            290                 295                 300

Asn Arg Glu Leu Val Ser Glu Leu Lys Arg Pro Pro Leu Cys Phe His
305                 310                 315                 320

Asn Gly Val Gln Tyr Lys Asn Asn Glu Glu Trp Thr Val Asp Ser Cys
            325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
            355                 360                 365

Cys Pro Arg Cys Trp Pro Ser Asp Ser Ala Asp Asp Gly Trp Ser Pro
            370                 375                 380

Trp Ser Glu Trp Thr Ser Cys Ser Ala Thr Cys Gly Asn Gly Ile Gln
385                 390                 395                 400

Gln Arg Gly Arg Ser Cys Asp Ser Leu Asn Asn Arg Cys Glu Gly Ser
            405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
            435                 440                 445

Val Thr Cys Gly Asp Gly Val Ile Thr Arg Ile Arg Leu Cys Asn Ser
            450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
            485                 490                 495

Pro Trp Ser Pro Trp Asp Ile Cys Ser Val Thr Cys Gly Gly Gly Val
            500                 505                 510
```

```
Gln Arg Arg Ser Arg Leu Cys Asn Asn Pro Thr Pro Gln Phe Gly Gly
            515                 520                 525

Lys Asp Cys Val Gly Asp Val Thr Glu Asn Gln Val Cys Asn Lys Gln
530                 535                 540

Asp Cys Pro Ile Asp Gly Cys Leu Ser Asn Pro Cys Phe Ala Gly Ala
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Lys Asp Val Asp Glu Cys
                580                 585                 590

Lys Glu Val Pro Asp Ala Cys Phe Asn His Asn Gly Glu His Arg Cys
            595                 600                 605

Lys Asn Thr Asp Pro Gly Tyr Asn Cys Leu Pro Cys Pro Pro Arg Phe
        610                 615                 620

Thr Gly Ser Gln Pro Phe Gly Arg Gly Val Glu His Ala Met Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
        675                 680                 685

Cys Gly Glu Asp Thr Asp Leu Asp Gly Trp Pro Asn Glu Asn Leu Val
        690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
            755                 760                 765

Asp Val Gly Asp Arg Cys Asp Asn Cys Pro Tyr Asn His Asn Pro Asp
770                 775                 780

Gln Ala Asp Thr Asp Lys Asn Gly Glu Gly Asp Ala Cys Ala Val Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
            820                 825                 830

Cys Asp Asn Cys Pro Leu Glu His Asn Pro Asp Gln Leu Asp Ser Asp
            835                 840                 845

Ser Asp Leu Ile Gly Asp Thr Cys Asp Asn Asn Gln Asp Ile Asp Glu
        850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Arg Asp Asn Cys Arg Leu
            900                 905                 910

Val Pro Asn Pro Asp Gln Lys Asp Ser Asp Gly Asp Gly Arg Gly Asp
        915                 920                 925

Ala Cys Lys Asp Asp Phe Asp His Asp Asn Val Pro Asp Ile Asp Asp
```

```
                     930               935                940
Ile Cys Pro Glu Asn Phe Asp Ile Ser Glu Thr Asp Phe Arg Arg Phe
945                 950                955                960

Gln Met Ile Pro Leu Asp Pro Lys Gly Thr Ser Gln Asn Asp Pro Asn
                965                970                975

Trp Val Val Arg His Gln Gly Lys Glu Leu Val Gln Thr Val Asn Cys
                    980                985                990

Asp Pro Gly Leu Ala Val Gly Tyr Asp Glu Phe Asn Ala Val Asp Phe
            995                1000               1005

Ser Gly Thr Phe Phe Ile Asn Thr Glu Arg Asp Asp Tyr Ala
        1010                1015               1020

Gly Phe Val Phe Gly Tyr Gln Ser Ser Arg Phe Tyr Val Val
        1025               1030               1035

Met Trp Lys Gln Val Thr Gln Ser Tyr Trp Asp Thr Asn Pro Thr
        1040               1045               1050

Arg Ala Gln Gly Tyr Ser Gly Leu Ser Val Lys Val Asn Ser
        1055               1060               1065

Thr Thr Gly Pro Gly Glu His Leu Arg Asn Ala Leu Trp His Thr
        1070               1075               1080

Gly Asn Thr Pro Gly Gln Val Arg Thr Leu Trp His Asp Pro Arg
        1085               1090               1095

His Ile Gly Trp Lys Asp Phe Thr Ala Tyr Arg Trp Arg Leu Ser
        1100               1105               1110

His Arg Pro Lys Thr Gly Tyr Ile Arg Val Val Met Tyr Glu Gly
        1115               1120               1125

Lys Lys Ile Met Ala Asp Ser Gly Pro Ile Tyr Asp Lys Thr Tyr
        1130               1135               1140

Ala Gly Gly Arg Leu Gly Leu Phe Val Phe Ser Gln Glu Met Val
        1145               1150               1155

Phe Phe Ser Asp Met Lys Tyr Glu Cys Arg Asp Ser
        1160               1165               1170

<210> SEQ ID NO 7
<211> LENGTH: 1170
<212> TYPE: PRT
<213> ORGANISM: Rattus norvegicus

<400> SEQUENCE: 7

Met Glu Leu Leu Arg Gly Leu Gly Val Leu Phe Leu Leu His Val Cys
1               5                   10                  15

Gly Ser Asn Arg Ile Pro Glu Ser Gly Gly Asp Asn Gly Val Phe Asp
                20                  25                  30

Ile Phe Glu Leu Ile Gly Gly Ala Arg Lys Val Pro Gly Arg Arg Leu
            35                  40                  45

Val Lys Gly Gln Asp Leu Ser Ser Pro Ala Phe Arg Ile Glu Asn Ala
        50                  55                  60

Asn Leu Ile Pro Pro Val Pro Asp Asp Lys Phe Gln Asp Leu Leu Asp
65                  70                  75                  80

Ala Val Trp Ala Asp Lys Gly Phe Ile Phe Leu Ala Ser Leu Arg Gln
                85                  90                  95

Met Lys Lys Thr Arg Gly Thr Leu Leu Ala Val Glu Arg Lys Asp Asn
                100                 105                 110

Ser Gly Gln Ile Phe Ser Val Val Ser Asn Gly Lys Ala Gly Thr Leu
            115                 120                 125
```

```
Asp Leu Ser Leu Ser Leu Pro Gly Lys Gln Gln Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Asp Lys Met Glu Ser
                165                 170                 175

Ala Glu Leu Asp Val Pro Ile Gln Ser Ile Phe Thr Arg Asp Leu Ala
            180                 185                 190

Asn Val Ala Arg Leu Arg Val Ala Lys Gly Asp Val Asn Asp Asn Phe
        195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Thr Asn Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Leu
            260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
    290                 295                 300

Asn Arg Glu Leu Ala Ser Glu Leu Arg Arg Pro Leu Cys Phe His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
        355                 360                 365

Cys Pro Arg Cys Trp Pro Ser Asp Ser Ala Asp Asp Gly Trp Ser Pro
    370                 375                 380

Trp Ser Glu Trp Thr Ser Cys Ser Ala Thr Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
    450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Ser
                485                 490                 495

Pro Trp Ser Leu Trp Asp Ile Cys Ser Val Thr Cys Gly Gly Gly Val
            500                 505                 510

Gln Arg Arg Ser Arg Leu Cys Asn Asn Pro Thr Pro Gln Phe Gly Gly
        515                 520                 525

Lys Asp Cys Val Gly Asp Val Thr Glu Asn Gln Val Cys Asn Lys Gln
    530                 535                 540

Asp Cys Pro Ile Asp Gly Cys Leu Ser Asn Pro Cys Phe Ala Gly Ala
```

```
545                 550                 555                 560
Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Lys Asp Val Asp Glu Cys
                580                 585                 590

Lys Glu Val Pro Asp Ala Cys Phe Asn His Asn Gly Glu His Arg Cys
                595                 600                 605

Lys Asn Thr Asp Pro Gly Tyr Asn Cys Leu Pro Cys Pro Pro Arg Phe
610                 615                 620

Thr Gly Ser Gln Pro Phe Gly Arg Gly Val Glu His Ala Met Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
                660                 665                 670

Met Tyr Arg Cys Glu Cys Lys Pro Gly Tyr Ala Gly Asn Gly Ile Ile
                675                 680                 685

Cys Gly Glu Asp Thr Asp Leu Asp Gly Trp Pro Asn Glu Asn Leu Val
690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
                740                 745                 750

Asn Cys Pro Phe His Tyr Asn Pro Ala Gln Tyr Asp Tyr Asp Arg Asp
                755                 760                 765

Asp Val Gly Asp Arg Cys Asp Asn Cys Pro Tyr Asn His Asn Pro Asp
                770                 775                 780

Gln Ala Asp Thr Asp Asn Asn Gly Glu Gly Asp Ala Cys Ala Val Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
                820                 825                 830

Cys Asp Asn Cys Pro Leu Glu His Asn Pro Asp Gln Leu Asp Ser Asp
                835                 840                 845

Ser Asp Arg Ile Gly Asp Thr Cys Asp Asn Asn Gln Ala Ile Asp Glu
850                 855                 860

Asp Gly His Gln Asn Asn Leu Glu Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Arg Asp Asn Cys Arg Leu
                900                 905                 910

Val Pro Asn Pro Asp Gln Lys Asp Ser Asp Gly Asp Gly Arg Gly Asp
                915                 920                 925

Ala Cys Lys Asp Asp Phe Asp His Asp Asn Val Pro Asp Ile Asp Asp
930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
                965                 970                 975
```

```
Trp Val Val Arg His Gln Gly Lys Glu Leu Val Gln Thr Val Asn Cys
            980                 985                 990

Asp Pro Gly Leu Ala Val Gly Tyr Asp Glu Phe Asn Ala Val Asp Phe
            995                 1000                1005

Ser Gly Thr Phe Phe Ile Asn Thr Glu Arg Asp Asp Tyr Ala
    1010                1015                1020

Gly Phe Val Phe Gly Tyr Gln Ser Ser Ser Arg Phe Tyr Val Val
    1025                1030                1035

Met Trp Lys Gln Val Thr Gln Ser Tyr Trp Asp Thr Asn Pro Thr
    1040                1045                1050

Arg Ala Gln Gly Tyr Ser Gly Leu Ser Val Lys Val Val Asn Ser
    1055                1060                1065

Thr Thr Gly Pro Gly Glu His Leu Arg Asn Ala Leu Trp His Thr
    1070                1075                1080

Gly Asn Thr Pro Gly Gln Val Arg Thr Leu Trp His Asp Pro Arg
    1085                1090                1095

His Ile Gly Trp Lys Asp Phe Thr Ala Tyr Arg Trp Arg Leu Ser
    1100                1105                1110

His Arg Pro Lys Thr Gly Leu Ile Arg Val Val Met Tyr Glu Gly
    1115                1120                1125

Lys Lys Ile Met Ala Asp Ser Gly Pro Ile Tyr Asp Lys Thr Tyr
    1130                1135                1140

Ala Gly Gly Arg Leu Gly Leu Phe Val Phe Ser Gln Glu Met Val
    1145                1150                1155

Phe Phe Ser Asp Met Lys Tyr Glu Cys Arg Asp Ser
    1160                1165                1170

<210> SEQ ID NO 8
<211> LENGTH: 6
<212> TYPE: PRT
<213> ORGANISM: Artificial sequence
<220> FEATURE:
<223> OTHER INFORMATION: TSP-1 fragment

<400> SEQUENCE: 8

Cys Ser Val Thr Cys Gly
1               5

<210> SEQ ID NO 9
<211> LENGTH: 11
<212> TYPE: PRT
<213> ORGANISM: Artificial sequence
<220> FEATURE:
<223> OTHER INFORMATION: 7N3 peptide

<400> SEQUENCE: 9

Phe Ile Arg Val Val Met Tyr Glu Gly Lys Lys
1               5                   10

<210> SEQ ID NO 10
<211> LENGTH: 13
<212> TYPE: PRT
<213> ORGANISM: Artificial sequence
<220> FEATURE:
<223> OTHER INFORMATION: CD47/IAP binding peptide

<400> SEQUENCE: 10

Arg Phe Tyr Val Val Met Trp Lys Gln Val Thr Gln Ser
1               5                   10
```

```
<210> SEQ ID NO 11
<211> LENGTH: 6
<212> TYPE: PRT
<213> ORGANISM: Artificial sequence
<220> FEATURE:
<223> OTHER INFORMATION: 4N1-2 peptide

<400> SEQUENCE: 11

Arg Phe Tyr Val Val Met
1               5

<210> SEQ ID NO 12
<211> LENGTH: 8
<212> TYPE: PRT
<213> ORGANISM: Artificial sequence
<220> FEATURE:
<223> OTHER INFORMATION: 4NGG

<400> SEQUENCE: 12

Arg Phe Tyr Gly Gly Met Trp Lys
1               5

<210> SEQ ID NO 13
<211> LENGTH: 11
<212> TYPE: PRT
<213> ORGANISM: Artificial sequence
<220> FEATURE:
<223> OTHER INFORMATION: 7NGG

<400> SEQUENCE: 13

Phe Ile Arg Gly Gly Met Tyr Glu Gly Lys Lys
1               5                   10
```